US00RE45744E

(19) United States
(12) Reissued Patent
Gale et al.

(10) Patent Number: US RE45,744 E
(45) Date of Reissued Patent: *Oct. 13, 2015

(54) TEMPERATURE CONTROLLED CRIMPING

(71) Applicant: Abbott Cardiovascular Systems Inc., Santa Clara, CA (US)

(72) Inventors: David C. Gale, Kennesaw, GA (US); Bin Huang, Pleasanton, CA (US); Anthony Abbate, Santa Clara, CA (US); Stephen D. Pacetti, San Jose, CA (US)

(73) Assignee: ABBOTT CARDIOVASCULAR SYSTEMS INC., Santa Clara, CA (US)

( * ) Notice: This patent is subject to a terminal disclaimer.

(21) Appl. No.: 14/074,543

(22) Filed: Nov. 7, 2013

Related U.S. Patent Documents

Reissue of:
(64) Patent No.: 8,052,912
Issued: Nov. 8, 2011
Appl. No.: 10/957,022
Filed: Oct. 1, 2004

U.S. Applications:
(63) Continuation-in-part of application No. 10/725,698, filed on Dec. 1, 2003.

(51) Int. Cl.
*A24B 5/00* (2006.01)
*A61F 2/958* (2013.01)
(Continued)

(52) U.S. Cl.
CPC ..... *A61F 2/958* (2013.01); *A61L 31/10* (2013.01); *A61L 31/14* (2013.01); *B29B 13/024* (2013.01);
(Continued)

(58) Field of Classification Search
CPC ..... A61F 2/958; A61L 31/10; A61L 31/14; B29B 13/024; Y10T 29/49865; B29C 65/56; B29C 65/76; B29C 66/91941; B29C 2035/0822; B29C 2071/022; B29C 66/9121; B29C 66/91; B29K 2001/10; B29K 2001/12; B29K 2023/00; B29K 2023/083; B29K 2023/086; B29K 2027/06; B29K 2027/08; B29K 2027/16; B29K 2029/00; B29K 2031/00; B29K 2033/08; B29K 2033/20; B29K 2055/02; B29K 2063/00; B29K 2075/00; B29K 2077/00; B29K 2083/00; B29L 2031/7542
See application file for complete search history.

(56) References Cited

U.S. PATENT DOCUMENTS 2,072,303 A 3/1937 Herrmann et al.
2,386,454 A 10/1945 Frosch et al.
(Continued)

FOREIGN PATENT DOCUMENTS

DE 42 24 401 1/1994
EP 0 301 856 2/1989
(Continued)

OTHER PUBLICATIONS

Angioplasty Summit Abstracts/Oral, The Am. J. of Cardiology, Apr. 23-26, 2013, p. 23B.
(Continued)

*Primary Examiner* — Elizabeth McKane
(74) *Attorney, Agent, or Firm* — Squire Patton Boggs (US) LLP

(57) ABSTRACT

This disclosure describes a method for crimping a polymeric stent onto a catheter for percutaneous transluminal coronary angioplasty or other intraluminal interventions. The method comprises crimping the stent onto a catheter when the polymer is at a target temperature other than ambient temperature. The polymer can optionally comprise drug(s).

8 Claims, 6 Drawing Sheets

(51) Int. Cl.

| | |
|---|---|
| ***A61L 31/10*** | (2006.01) |
| ***A61L 31/14*** | (2006.01) |
| ***B29B 13/02*** | (2006.01) |
| ***B29C 65/00*** | (2006.01) |
| *B29C 65/76* | (2006.01) |
| *B29C 65/56* | (2006.01) |
| *B29C 35/08* | (2006.01) |
| *B29C 71/02* | (2006.01) |
| *B29K 1/00* | (2006.01) |
| *B29K 23/00* | (2006.01) |
| *B29K 27/06* | (2006.01) |
| *B29K 27/00* | (2006.01) |
| *B29K 29/00* | (2006.01) |
| *B29K 31/00* | (2006.01) |
| *B29K 33/00* | (2006.01) |
| *B29K 33/20* | (2006.01) |
| *B29K 55/02* | (2006.01) |
| *B29K 63/00* | (2006.01) |
| *B29K 75/00* | (2006.01) |
| *B29K 77/00* | (2006.01) |
| *B29K 83/00* | (2006.01) |
| *B29L 31/00* | (2006.01) |
| *A61F 2/95* | (2013.01) |

(52) U.S. Cl.

CPC ... *B29C 66/91941* (2013.01); *A61F 2002/9522* (2013.01); *B29C 65/56* (2013.01); *B29C 65/76* (2013.01); *B29C 66/919* (2013.01); *B29C 66/9121* (2013.01); *B29C 66/91431* (2013.01); *B29C 66/91641* (2013.01); *B29C 66/91921* (2013.01); *B29C 66/91945* (2013.01); *B29C 2035/0822* (2013.01); *B29C 2071/022* (2013.01); *B29K 2001/00* (2013.01); *B29K 2001/12* (2013.01); *B29K 2023/00* (2013.01); *B29K 2023/083* (2013.01); *B29K 2023/086* (2013.01); *B29K 2027/06* (2013.01); *B29K 2027/08* (2013.01); *B29K 2027/16* (2013.01); *B29K 2029/00* (2013.01); *B29K 2031/00* (2013.01); *B29K 2033/08* (2013.01); *B29K 2033/20* (2013.01); *B29K 2055/02* (2013.01); *B29K 2063/00* (2013.01); *B29K 2075/00* (2013.01); *B29K 2077/00* (2013.01); *B29K 2083/00* (2013.01); *B29L 2031/7542* (2013.01); *Y10T 29/49865* (2013.01); *Y10T 428/24942* (2015.01)

(56) References Cited

U.S. PATENT DOCUMENTS

| | | | |
|---|---|---|---|
| 3,178,399 | A | 4/1965 | Lo |
| 3,773,737 | A | 11/1973 | Goodman et al. |
| 3,849,514 | A | 11/1974 | Gray, Jr. et al. |
| 3,855,638 | A | 12/1974 | Pilliar |
| 3,929,992 | A | 12/1975 | Sehgal et al. |
| 4,101,984 | A | 7/1978 | MacGregor |
| 4,151,413 | A | 4/1979 | Arnold |
| 4,226,243 | A | 10/1980 | Shalaby et al. |
| 4,316,885 | A | 2/1982 | Rakhit |
| 4,321,711 | A | 3/1982 | Mano |
| 4,325,903 | A | 4/1982 | Wissbrun et al. |
| 4,329,383 | A | 5/1982 | Joh |
| 4,343,931 | A | 8/1982 | Barrows |
| 4,355,426 | A | 10/1982 | MacGregor |
| 4,374,669 | A | 2/1983 | MacGregor |
| 4,459,252 | A | 7/1984 | MacGregor |
| 4,529,792 | A | 7/1985 | Barrows |
| 4,611,051 | A | 9/1986 | Hayes et al. |
| 4,650,803 | A | 3/1987 | Stella et al. |
| 4,656,242 | A | 4/1987 | Swan et al. |
| 4,693,721 | A | 9/1987 | Ducheyne |
| 4,729,871 | A | 3/1988 | Morimoto |
| 4,733,665 | A | 3/1988 | Palmaz |
| 4,800,882 | A | 1/1989 | Gianturco |
| 4,816,339 | A | 3/1989 | Tu et al. |
| 4,882,168 | A | 11/1989 | Casey et al. |
| 4,886,062 | A | 12/1989 | Wiktor |
| 4,931,287 | A | 6/1990 | Bae et al. |
| 4,941,870 | A | 7/1990 | Okada et al. |
| 4,977,901 | A | 12/1990 | Ofstead |
| 5,019,096 | A | 5/1991 | Fox, Jr. et al. |
| 5,059,211 | A | 10/1991 | Stack et al. |
| 5,100,883 | A | 3/1992 | Schiehser |
| 5,100,992 | A | 3/1992 | Cohn et al. |
| 5,102,876 | A | 4/1992 | Caufield |
| 5,112,457 | A | 5/1992 | Marchant |
| 5,118,677 | A | 6/1992 | Caufield |
| 5,118,678 | A | 6/1992 | Kao et al. |
| 5,120,725 | A | 6/1992 | Kao et al. |
| 5,120,727 | A | 6/1992 | Kao et al. |
| 5,120,842 | A | 6/1992 | Failli et al. |
| 5,133,742 | A | 7/1992 | Pinchuk |
| 5,138,051 | A | 8/1992 | Hughes et al. |
| 5,151,413 | A | 9/1992 | Caufield et al. |
| 5,162,333 | A | 11/1992 | Failli et al. |
| 5,163,952 | A | 11/1992 | Froix |
| 5,163,958 | A | 11/1992 | Pinchuk |
| 5,165,919 | A | 11/1992 | Sasaki et al. |
| 5,169,851 | A | 12/1992 | Hughes et al. |
| 5,219,980 | A | 6/1993 | Swidler |
| 5,221,740 | A | 6/1993 | Hughes |
| 5,234,456 | A | 8/1993 | Silvestrini |
| 5,258,020 | A | 11/1993 | Froix |
| 5,258,389 | A | 11/1993 | Goulet et al. |
| 5,272,012 | A | 12/1993 | Opolski |
| 5,292,516 | A | 3/1994 | Viegas et al. |
| 5,298,260 | A | 3/1994 | Viegas et al. |
| 5,300,295 | A | 4/1994 | Viegas et al. |
| 5,306,286 | A | 4/1994 | Stack et al. |
| 5,306,501 | A | 4/1994 | Viegas et al. |
| 5,306,786 | A | 4/1994 | Moens et al. |
| 5,328,471 | A | 7/1994 | Slepian |
| 5,330,768 | A | 7/1994 | Park et al. |
| 5,344,833 | A | 9/1994 | Hughes |
| 5,370,682 | A | 12/1994 | Schmitt |
| 5,370,684 | A | 12/1994 | Vallana et al. |
| 5,380,299 | A | 1/1995 | Fearnot et al. |
| 5,383,928 | A | 1/1995 | Scott et al. |
| 5,417,981 | A | 5/1995 | Endo et al. |
| 5,419,760 | A | 5/1995 | Narciso, Jr. |
| 5,433,909 | A | 7/1995 | Martakos et al. |
| 5,437,834 | A | 8/1995 | Okimatsu et al. |
| 5,441,515 | A | 8/1995 | Khosravi et al. |
| 5,447,724 | A | 9/1995 | Helmus et al. |
| 5,455,040 | A | 10/1995 | Marchant |
| 5,462,990 | A | 10/1995 | Hubbell et al. |
| 5,464,650 | A | 11/1995 | Berg et al. |
| 5,468,253 | A | 11/1995 | Bezwada et al. |
| 5,480,599 | A | 1/1996 | Leven et al. |
| 5,485,496 | A | 1/1996 | Lee et al. |
| 5,492,768 | A | 2/1996 | Okimatsu et al. |
| 5,516,781 | A | 5/1996 | Morris et al. |
| 5,516,881 | A | 5/1996 | Lee et al. |
| 5,522,894 | A | 6/1996 | Draenert |
| 5,527,337 | A | 6/1996 | Stack et al. |
| 5,527,907 | A | 6/1996 | Or et al. |
| 5,563,145 | A | 10/1996 | Failli |
| 5,569,463 | A | 10/1996 | Helmus et al. |
| 5,571,187 | A | 11/1996 | Devanathan |
| 5,575,818 | A | 11/1996 | Pinchuk |
| 5,578,073 | A | 11/1996 | Haimovich et al. |
| 5,583,139 | A | 12/1996 | Or et al. |
| 5,584,877 | A | 12/1996 | Miyake et al. |
| 5,605,693 | A | 2/1997 | Seare, Jr. |
| 5,605,696 | A | 2/1997 | Eury et al. |
| 5,607,463 | A | 3/1997 | Schwartz et al. |
| 5,607,467 | A | 3/1997 | Froix |
| 5,609,629 | A | 3/1997 | Fearnot et al. |

(56) References Cited

U.S. PATENT DOCUMENTS 5,610,241 A 3/1997 Lee et al.
5,616,338 A 4/1997 Fox, Jr. et al.
5,624,411 A 4/1997 Tuch
5,628,730 A 5/1997 Shapland et al.
5,630,840 A 5/1997 Mayer
5,632,779 A 5/1997 Davidson
5,644,020 A 7/1997 Timmermann et al.
5,649,977 A 7/1997 Campbell
5,651,174 A * 7/1997 Schwartz et al. ..... 29/527.2
5,658,995 A 8/1997 Kohn et al.
5,665,772 A 9/1997 Cottens et al.
5,667,767 A 9/1997 Greff et al.
5,670,161 A 9/1997 Healy et al.
5,670,558 A 9/1997 Onishi et al.
5,672,605 A 9/1997 Or et al.
5,674,242 A 10/1997 Phan et al.
5,679,400 A 10/1997 Tuch
5,697,967 A 12/1997 Dinh et al.
5,700,286 A 12/1997 Tartaglia et al.
5,702,754 A 12/1997 Zhong
5,707,385 A 1/1998 Williams
5,707,867 A 1/1998 Glenn
5,711,958 A 1/1998 Cohn et al.
5,713,949 A 2/1998 Jayaraman
5,716,981 A 2/1998 Hunter et al.
5,721,131 A 2/1998 Rudolph et al.
5,723,219 A 3/1998 Kolluri et al.
5,725,567 A 3/1998 Wolff et al.
5,735,897 A 4/1998 Buirge
5,746,691 A 5/1998 Frantzen
5,746,998 A 5/1998 Torchilin et al.
5,755,771 A 5/1998 Penn et al.
5,759,192 A 6/1998 Saunders
5,759,205 A 6/1998 Valentini
5,766,710 A 6/1998 Turnlund et al.
5,769,883 A 6/1998 Buscemi et al.
5,776,184 A 7/1998 Tuch
5,783,657 A 7/1998 Pavlin et al.
5,788,558 A 8/1998 Klein
5,788,979 A 8/1998 Alt et al.
5,795,318 A 8/1998 Wang et al.
5,798,355 A 8/1998 Steiner et al.
5,800,392 A 9/1998 Racchini
5,800,512 A 9/1998 Lentz et al.
5,820,917 A 10/1998 Tuch
5,824,048 A 10/1998 Tuch
5,824,049 A 10/1998 Ragheb et al.
5,830,178 A 11/1998 Jones et al.
5,836,965 A 11/1998 Jendersee et al.
5,837,008 A 11/1998 Berg et al.
5,837,313 A 11/1998 Ding et al.
5,843,172 A 12/1998 Yan
5,843,960 A 12/1998 Steiner et al.
5,846,981 A 12/1998 Steiner et al.
5,849,859 A 12/1998 Acemoglu
5,851,508 A 12/1998 Greff et al.
5,854,376 A 12/1998 Higashi
5,856,814 A 1/1999 Yagyu
5,858,746 A 1/1999 Hubbell et al.
5,865,814 A 2/1999 Tuch
5,869,127 A 2/1999 Zhong
5,873,904 A 2/1999 Ragheb et al.
5,876,433 A 3/1999 Lunn
5,877,224 A 3/1999 Brocchini et al.
5,879,398 A 3/1999 Swarts et al.
5,879,713 A 3/1999 Roth et al.
5,897,911 A 4/1999 Loeffler
5,898,029 A 4/1999 Lyons et al.
5,902,875 A 5/1999 Roby et al.
5,905,168 A 5/1999 Dos Santos et al.
5,910,564 A 6/1999 Gruning et al.
5,912,253 A 6/1999 Cottens et al.
5,914,387 A 6/1999 Roby et al.
5,919,893 A 7/1999 Roby et al.
5,925,720 A 7/1999 Kataoka et al.
5,928,279 A 7/1999 Shannon et al.
5,932,243 A 8/1999 Fricker et al.
5,932,299 A 8/1999 Katoot
5,945,029 A 8/1999 Scholz et al.
5,955,509 A 9/1999 Webber et al.
5,958,385 A 9/1999 Tondeur et al.
5,961,914 A 10/1999 Mannion et al.
5,962,007 A 10/1999 Cooper et al.
5,962,138 A 10/1999 Kolluri et al.
5,968,091 A * 10/1999 Pinchuk et al. ..... 623/1.16
5,971,954 A 10/1999 Conway et al.
5,972,027 A 10/1999 Johnson
5,980,564 A 11/1999 Stinson et al.
5,980,928 A 11/1999 Terry
5,980,972 A 11/1999 Ding
5,985,890 A 11/1999 Cottens et al.
5,994,444 A 11/1999 Trescony et al.
5,997,517 A 12/1999 Whitbourne
6,001,117 A 12/1999 Huxel et al.
6,010,529 A 1/2000 Herweck et al.
6,010,530 A 1/2000 Goicoechea
6,011,125 A 1/2000 Lohmeijer et al.
6,013,621 A 1/2000 Nishi et al.
6,015,541 A 1/2000 Greff et al.
6,015,815 A 1/2000 Mollison
6,027,779 A 2/2000 Campbell et al.
6,033,582 A 3/2000 Lee et al.
6,034,204 A 3/2000 Mohr et al.
6,042,875 A 3/2000 Ding et al.
6,051,576 A 4/2000 Ashton et al.
6,051,648 A 4/2000 Rhee et al.
6,054,553 A 4/2000 Groth et al.
6,056,906 A 5/2000 Werneth et al.
6,056,993 A 5/2000 Leidner et al.
6,060,451 A 5/2000 DiMaio et al.
6,060,518 A 5/2000 Kabanov et al.
6,066,156 A 5/2000 Yan
6,080,488 A 6/2000 Hostettler et al.
6,083,534 A 7/2000 Wallach et al.
6,095,817 A 8/2000 Wagner et al.
6,096,070 A 8/2000 Ragheb et al.
6,099,562 A 8/2000 Ding et al.
6,100,346 A 8/2000 Jamiolkowski et al.
6,110,188 A 8/2000 Narciso, Jr.
6,110,483 A 8/2000 Whitbourne et al.
6,113,629 A 9/2000 Ken
6,120,491 A 9/2000 Kohn et al.
6,120,536 A 9/2000 Ding et al.
6,120,788 A 9/2000 Barrows
6,120,847 A 9/2000 Yang et al.
6,120,904 A 9/2000 Hostettler et al.
6,121,027 A 9/2000 Clapper et al.
6,129,761 A 10/2000 Hubbell
6,136,333 A 10/2000 Cohn et al.
6,139,573 A 10/2000 Sogard et al.
6,143,037 A 11/2000 Goldstein et al.
6,143,354 A 11/2000 Koulik et al.
6,143,370 A 11/2000 Panagiotou et al.
6,153,252 A 11/2000 Hossainy et al.
6,159,978 A 12/2000 Myers et al.
6,165,210 A 12/2000 Lau et al.
6,165,212 A 12/2000 Dereume et al.
6,172,167 B1 1/2001 Stapert et al.
6,177,523 B1 1/2001 Reich et al.
6,180,632 B1 1/2001 Myers et al.
6,200,985 B1 3/2001 Cottens et al.
6,203,551 B1 3/2001 Wu
6,206,915 B1 3/2001 Fagan et al.
6,211,249 B1 4/2001 Cohn et al.
6,214,901 B1 4/2001 Chudzik et al.
6,221,102 B1 * 4/2001 Baker et al. ..... 623/1.36
6,228,934 B1 5/2001 Horowitz et al.
6,231,600 B1 5/2001 Zhong
6,240,616 B1 6/2001 Yan
6,245,753 B1 6/2001 Byun et al.
6,245,760 B1 6/2001 He et al.
6,248,129 B1 6/2001 Froix
6,251,136 B1 6/2001 Guruwaiya et al.
6,254,632 B1 7/2001 Wu et al.

(56) References Cited

U.S. PATENT DOCUMENTS 6,258,121 B1 7/2001 Yang et al.
6,258,371 B1 7/2001 Koulik et al.
6,262,034 B1 7/2001 Mathiowitz et al.
6,270,788 B1 8/2001 Koulik et al.
6,273,913 B1 8/2001 Wright et al.
6,277,449 B1 8/2001 Kolluri et al.
6,281,225 B1 8/2001 Hearst et al.
6,283,947 B1 9/2001 Mirzaee
6,283,949 B1 9/2001 Roorda
6,284,305 B1 9/2001 Ding et al.
6,284,788 B1 9/2001 Mittendorf et al.
6,287,337 B1 9/2001 Martakos et al.
6,287,628 B1 9/2001 Hossainy et al.
6,293,959 B1 9/2001 Miller et al.
6,299,604 B1 10/2001 Ragheb et al.
6,306,176 B1 10/2001 Whitbourne
6,309,402 B1 10/2001 Jendersee et al.
6,331,313 B1 12/2001 Wong et al.
6,335,029 B1 1/2002 Kamath et al.
6,344,035 B1 2/2002 Chudzik et al.
6,346,110 B2 2/2002 Wu
6,358,556 B1 3/2002 Ding et al.
6,364,903 B2 4/2002 Tseng et al.
6,368,346 B1 * 4/2002 Jadhav ..... 623/1.22
6,368,658 B1 4/2002 Schwarz et al.
6,379,379 B1 4/2002 Wang
6,379,381 B1 4/2002 Hossainy et al.
6,384,046 B1 5/2002 Schuler et al.
6,387,124 B1 5/2002 Buscemi et al.
6,387,379 B1 5/2002 Goldberg et al.
6,395,326 B1 5/2002 Castro et al.
6,406,739 B1 6/2002 LeBoeuf et al.
6,419,692 B1 7/2002 Yang et al.
6,451,373 B1 9/2002 Hossainy et al.
6,475,235 B1 11/2002 Jayaraman
6,482,834 B2 11/2002 Spada et al.
6,494,862 B1 12/2002 Ray et al.
6,503,538 B1 1/2003 Chu et al.
6,503,556 B2 1/2003 Harish et al.
6,503,954 B1 1/2003 Bhat et al.
6,506,437 B1 1/2003 Harish et al.
6,524,347 B1 2/2003 Myers et al.
6,527,801 B1 3/2003 Dutta
6,527,863 B1 3/2003 Pacetti et al.
6,528,526 B1 3/2003 Myers et al.
6,530,950 B1 3/2003 Alvarado et al.
6,530,951 B1 3/2003 Bates et al.
6,540,776 B2 4/2003 Sanders Millare et al.
6,544,223 B1 4/2003 Kokish
6,544,543 B1 4/2003 Mandrusov et al.
6,544,582 B1 4/2003 Yoe
6,547,819 B2 4/2003 Strecker
6,555,157 B1 4/2003 Hossainy
6,558,733 B1 5/2003 Hossainy et al.
6,565,659 B1 5/2003 Pacetti et al.
6,572,644 B1 6/2003 Moein
6,574,497 B1 6/2003 Pacetti
6,585,755 B2 7/2003 Jackson et al.
6,585,765 B1 7/2003 Hossainy et al.
6,585,926 B1 7/2003 Mirzaee
6,605,154 B1 8/2003 Villareal
6,610,087 B1 8/2003 Zarbatany et al.
6,616,765 B1 9/2003 Castro et al.
6,623,448 B2 9/2003 Slater
6,623,764 B1 9/2003 Sokoll et al.
6,625,486 B2 9/2003 Lundkvist et al.
6,629,350 B2 10/2003 Motsenbocker
6,645,135 B1 11/2003 Bhat
6,645,195 B1 11/2003 Bhat et al.
6,652,581 B1 11/2003 Ding
6,656,216 B1 12/2003 Hossainy et al.
6,656,506 B1 12/2003 Wu et al.
6,660,034 B1 12/2003 Mandrusov et al.
6,663,662 B2 12/2003 Pacetti et al.
6,663,880 B1 12/2003 Roorda et al.
6,666,880 B1 12/2003 Chiu et al.
6,673,154 B1 1/2004 Pacetti et al.
6,673,385 B1 1/2004 Ding et al.
6,689,099 B2 2/2004 Mirzaee
6,695,920 B1 2/2004 Pacetti et al.
6,706,013 B1 3/2004 Bhat et al.
6,709,514 B1 3/2004 Hossainy
6,712,845 B2 3/2004 Hossainy
6,713,119 B2 3/2004 Hossainy et al.
6,716,444 B1 4/2004 Castro et al.
6,723,120 B2 4/2004 Yan
6,733,768 B2 5/2004 Hossainy et al.
6,739,033 B2 5/2004 Hijlkema et al.
6,740,040 B1 5/2004 Mandrusov et al.
6,743,462 B1 6/2004 Pacetti
6,746,773 B2 6/2004 Llanos et al.
6,749,626 B1 6/2004 Bhat et al.
6,753,071 B1 6/2004 Pacetti et al.
6,758,859 B1 7/2004 Dang et al.
6,759,054 B2 7/2004 Chen et al.
6,764,505 B1 7/2004 Hossainy et al.
6,783,543 B2 8/2004 Jang
6,790,228 B2 9/2004 Hossainy et al.
6,823,576 B2 11/2004 Austin
6,861,088 B2 3/2005 Weber et al.
6,865,810 B2 3/2005 Stinson
6,869,443 B2 3/2005 Buscemi et al.
6,878,160 B2 4/2005 Gilligan et al.
6,887,270 B2 5/2005 Miller et al.
6,887,485 B2 5/2005 Fitzhugh et al.
6,890,546 B2 5/2005 Mollison et al.
6,899,731 B2 5/2005 Li et al.
6,948,223 B2 9/2005 Shortt
7,010,850 B2 3/2006 Hijlkema et al.
7,077,859 B2 7/2006 Sirhan et al.
7,291,165 B2 11/2007 Rosenthal et al.
7,316,148 B2 1/2008 Asmus et al.
7,591,844 B2 9/2009 Llanos et al.
7,682,647 B2 3/2010 Hossainy et al.
8,123,793 B2 2/2012 Roach et al.
2001/0007083 A1 7/2001 Roorda
2001/0014717 A1 8/2001 Hossainy et al.
2001/0018469 A1 8/2001 Chen et al.
2001/0020011 A1 9/2001 Mathiowitz et al.
2001/0029351 A1 10/2001 Falotico et al.
2001/0037145 A1 11/2001 Guruwaiya et al.
2001/0046518 A1 11/2001 Sawhney
2001/0051608 A1 12/2001 Mathiowitz et al.
2002/0005206 A1 1/2002 Falotico et al.
2002/0007213 A1 1/2002 Falotico et al.
2002/0007214 A1 1/2002 Falotico
2002/0007215 A1 1/2002 Falotico et al.
2002/0009604 A1 1/2002 Zamora et al.
2002/0016625 A1 2/2002 Falotico et al.
2002/0032414 A1 3/2002 Ragheb et al.
2002/0032434 A1 3/2002 Chudzik et al.
2002/0035774 A1 3/2002 Austin
2002/0038145 A1 3/2002 Jang
2002/0051730 A1 5/2002 Bodnar et al.
2002/0071822 A1 6/2002 Uhrich
2002/0077693 A1 6/2002 Barclay et al.
2002/0082679 A1 6/2002 Sirhan et al.
2002/0082685 A1 6/2002 Sirhan et al.
2002/0087123 A1 7/2002 Hossainy et al.
2002/0091433 A1 7/2002 Ding et al.
2002/0094440 A1 7/2002 Llanos et al.
2002/0100998 A1 8/2002 Hock et al.
2002/0111590 A1 8/2002 Davila et al.
2002/0120326 A1 8/2002 Michal
2002/0123801 A1 9/2002 Pacetti et al.
2002/0127263 A1 9/2002 Carlyle et al.
2002/0142039 A1 10/2002 Claude
2002/0143382 A1 10/2002 Hijlkema et al.
2002/0155212 A1 10/2002 Hossainy
2002/0165608 A1 11/2002 Llanos et al.
2002/0176849 A1 11/2002 Slepian
2002/0183581 A1 12/2002 Yoe et al.
2002/0188037 A1 12/2002 Chudzik et al.
2002/0188277 A1 12/2002 Roorda et al.

(56) References Cited

U.S. PATENT DOCUMENTS

| | | | |
|---|---|---|---|
| 2003/0004141 | A1 | 1/2003 | Brown |
| 2003/0028243 | A1 | 2/2003 | Bates et al. |
| 2003/0028244 | A1 | 2/2003 | Bates et al. |
| 2003/0031780 | A1 | 2/2003 | Chudzik et al. |
| 2003/0032767 | A1 | 2/2003 | Tada et al. |
| 2003/0036794 | A1 | 2/2003 | Ragheb et al. |
| 2003/0039689 | A1 | 2/2003 | Chen et al. |
| 2003/0040712 | A1 | 2/2003 | Ray et al. |
| 2003/0040790 | A1 | 2/2003 | Furst |
| 2003/0059520 | A1 | 3/2003 | Chen et al. |
| 2003/0060877 | A1 | 3/2003 | Falotico et al. |
| 2003/0065377 | A1 | 4/2003 | Davila et al. |
| 2003/0072868 | A1 | 4/2003 | Harish et al. |
| 2003/0073961 | A1 | 4/2003 | Happ |
| 2003/0083646 | A1 | 5/2003 | Sirhan et al. |
| 2003/0083739 | A1 | 5/2003 | Cafferata |
| 2003/0097088 | A1 | 5/2003 | Pacetti |
| 2003/0097173 | A1 | 5/2003 | Dutta |
| 2003/0099712 | A1 | 5/2003 | Jayaraman |
| 2003/0105518 | A1 | 6/2003 | Dutta |
| 2003/0113439 | A1 | 6/2003 | Pacetti et al. |
| 2003/0144727 | A1 | 7/2003 | Rosenthal et al. |
| 2003/0150380 | A1 | 8/2003 | Yoe |
| 2003/0157241 | A1 | 8/2003 | Hossainy et al. |
| 2003/0158517 | A1 | 8/2003 | Kokish |
| 2003/0190406 | A1 | 10/2003 | Hossainy et al. |
| 2003/0207020 | A1 | 11/2003 | Villareal |
| 2003/0208254 | A1 | 11/2003 | Shortt |
| 2003/0211230 | A1 | 11/2003 | Pacetti et al. |
| 2004/0018296 | A1 | 1/2004 | Castro et al. |
| 2004/0029952 | A1 | 2/2004 | Chen et al. |
| 2004/0047978 | A1 | 3/2004 | Hossainy et al. |
| 2004/0047980 | A1 | 3/2004 | Pacetti et al. |
| 2004/0052858 | A1 | 3/2004 | Wu et al. |
| 2004/0052859 | A1 | 3/2004 | Wu et al. |
| 2004/0054104 | A1 | 3/2004 | Pacetti |
| 2004/0060508 | A1 | 4/2004 | Pacetti et al. |
| 2004/0062853 | A1 | 4/2004 | Pacetti et al. |
| 2004/0063805 | A1 | 4/2004 | Pacetti et al. |
| 2004/0071861 | A1 | 4/2004 | Mandrusov et al. |
| 2004/0072922 | A1 | 4/2004 | Hossainy et al. |
| 2004/0073298 | A1 | 4/2004 | Hossainy |
| 2004/0086542 | A1 | 5/2004 | Hossainy et al. |
| 2004/0086550 | A1 | 5/2004 | Roorda et al. |
| 2004/0096504 | A1 | 5/2004 | Michal |
| 2004/0098117 | A1 | 5/2004 | Hossainy et al. |
| 2004/0220665 | A1 | 11/2004 | Hossainy et al. |
| 2005/0037052 | A1 | 2/2005 | Udipi et al. |
| 2005/0038134 | A1 | 2/2005 | Loomis et al. |
| 2005/0038497 | A1 | 2/2005 | Neuendorf et al. |
| 2005/0043786 | A1 | 2/2005 | Chu et al. |
| 2005/0049693 | A1 | 3/2005 | Walker |
| 2005/0049694 | A1 | 3/2005 | Neary |
| 2005/0054774 | A1 | 3/2005 | Kangas |
| 2005/0055044 | A1 | 3/2005 | Kangas |
| 2005/0055078 | A1 | 3/2005 | Campbell |
| 2005/0060020 | A1 | 3/2005 | Jenson |
| 2005/0064088 | A1 | 3/2005 | Fredrickson |
| 2005/0065501 | A1 | 3/2005 | Wallace |
| 2005/0065545 | A1 | 3/2005 | Wallace |
| 2005/0065593 | A1 | 3/2005 | Chu et al. |
| 2005/0074406 | A1 | 4/2005 | Couvillon, Jr. et al. |
| 2005/0074545 | A1 | 4/2005 | Thomas |
| 2005/0075714 | A1 | 4/2005 | Cheng et al. |
| 2005/0079274 | A1 | 4/2005 | Palasis et al. |
| 2005/0084515 | A1 | 4/2005 | Udipi et al. |
| 2005/0106210 | A1 | 5/2005 | Ding et al. |
| 2005/0113903 | A1 | 5/2005 | Rosenthal et al. |
| 2005/0118344 | A1 | 6/2005 | Pacetti |
| 2005/0119720 | A1 | 6/2005 | Gale et al. |
| 2005/0143752 | A1 | 6/2005 | Schwager et al. |
| 2005/0233062 | A1 | 10/2005 | Hossainy et al. |
| 2005/0238686 | A1 | 10/2005 | Hossainy et al. |
| 2007/0289117 | A1 | 12/2007 | Huang et al. |

FOREIGN PATENT DOCUMENTS

| | | |
|---|---|---|
| EP | 0 323 042 | 7/1989 |
| EP | 0 396 429 | 11/1990 |
| EP | 0 401 747 | 12/1990 |
| EP | 0 414 632 | 2/1991 |
| EP | 0 475 230 | 3/1992 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 687 008 | 12/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 875 218 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 950 386 | 10/1999 |
| EP | 0 953 320 | 11/1999 |
| EP | 0 970 711 | 1/2000 |
| EP | 0 978 288 | 2/2000 |
| EP | 0 982 041 | 3/2000 |
| EP | 1 023 879 | 8/2000 |
| EP | 1 036 562 | 9/2000 |
| EP | 1 064 942 | 1/2001 |
| EP | 1 192 957 | 4/2002 |
| EP | 1 273 314 | 1/2003 |
| EP | 1 470 830 | 5/2004 |
| EP | 1 440 699 | 7/2004 |
| FR | 2 785 812 | 5/2000 |
| JP | 63-160645 | 7/1988 |
| JP | 3-14516 | 1/1991 |
| JP | 4-215768 | 8/1992 |
| JP | 8-33718 | 2/1996 |
| JP | 8-21306 | 8/1996 |
| JP | 9-85028 | 3/1997 |
| JP | 10-305105 | 11/1998 |
| JP | 11299901 | 11/1999 |
| JP | 2000-051367 | 2/2000 |
| JP | 2001-190687 | 7/2001 |
| JP | 2003-210570 | 7/2003 |
| JP | 2004-523275 | 8/2004 |
| JP | 2005-512959 | 5/2005 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 90/01969 | 3/1990 |
| WO | WO 91/12846 | 9/1991 |
| WO | WO 94/09760 | 5/1994 |
| WO | WO 94/13268 | 6/1994 |
| WO | WO 95/10989 | 4/1995 |
| WO | WO 95/11817 | 5/1995 |
| WO | WO 95/24929 | 9/1995 |
| WO | WO 95/31104 | 11/1995 |
| WO | WO 96/13273 | 5/1996 |
| WO | WO 96/28115 | 9/1996 |
| WO | WO 96/40140 | 12/1996 |
| WO | WO 96/40174 | 12/1996 |
| WO | WO 97/03654 | 2/1997 |
| WO | WO 97/10011 | 3/1997 |
| WO | WO 97/29793 | 8/1997 |
| WO | WO 97/31020 | 8/1997 |
| WO | WO 97/45105 | 12/1997 |
| WO | WO 97/46590 | 12/1997 |
| WO | WO 98/02441 | 1/1998 |
| WO | WO 98/04256 | 2/1998 |
| WO | WO 98/08463 | 3/1998 |
| WO | WO 98/09523 | 3/1998 |
| WO | WO 98/10747 | 3/1998 |
| WO | WO 98/17331 | 4/1998 |
| WO | WO 98/23228 | 6/1998 |

(56) References Cited

FOREIGN PATENT DOCUMENTS

| | | |
|---|---|---|
| WO | WO 98/32398 | 7/1998 |
| WO | WO 98/36784 | 8/1998 |
| WO | WO 98/38687 | 9/1998 |
| WO | WO 98/44921 | 10/1998 |
| WO | WO 98/44922 | 10/1998 |
| WO | WO 99/01118 | 1/1999 |
| WO | WO 99/16386 | 4/1999 |
| WO | WO 99/19471 | 4/1999 |
| WO | WO 99/19473 | 4/1999 |
| WO | WO 99/24036 | 5/1999 |
| WO | WO 99/38546 | 8/1999 |
| WO | WO 99/39720 | 8/1999 |
| WO | WO 99/42104 | 8/1999 |
| WO | WO 99/44584 | 9/1999 |
| WO | WO 99/44597 | 9/1999 |
| WO | WO 99/60997 | 12/1999 |
| WO | WO 99/61040 | 12/1999 |
| WO | WO 99/63981 | 12/1999 |
| WO | WO 00/02599 | 1/2000 |
| WO | WO 00/09085 | 2/2000 |
| WO | WO 00/12147 | 3/2000 |
| WO | WO 00/15208 | 3/2000 |
| WO | WO 00/18446 | 4/2000 |
| WO | WO 00/24390 | 5/2000 |
| WO | WO 00/32234 | 6/2000 |
| WO | WO 00/32238 | 6/2000 |
| WO | WO 00/33878 | 6/2000 |
| WO | WO 00/38590 | 7/2000 |
| WO | WO 00/38703 | 7/2000 |
| WO | WO 00/38754 | 7/2000 |
| WO | WO 00/42949 | 7/2000 |
| WO | WO 00/56247 | 9/2000 |
| WO | WO 00/57818 | 10/2000 |
| WO | WO 00/64506 | 11/2000 |
| WO | WO 00/66122 | 11/2000 |
| WO | WO 00/71052 | 11/2000 |
| WO | WO 00/74665 | 12/2000 |
| WO | WO 01/01890 | 1/2001 |
| WO | WO 01/14387 | 3/2001 |
| WO | WO 01/15751 | 3/2001 |
| WO | WO 01/17577 | 3/2001 |
| WO | WO 01/23395 | 4/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 01/87372 | 11/2001 |
| WO | WO 01/87373 | 11/2001 |
| WO | WO 02/03890 | 1/2002 |
| WO | WO 02/26139 | 4/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/074194 | 9/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/035131 | 5/2003 |
| WO | WO 03/037223 | 5/2003 |
| WO | WO 03/309612 | 5/2003 |
| WO | WO 03/080147 | 10/2003 |
| WO | WO 03/082368 | 10/2003 |
| WO | WO 03/090818 | 11/2003 |
| WO | WO 03/097015 | 11/2003 |
| WO | WO 2004/000383 | 12/2003 |
| WO | WO 2004/009145 | 1/2004 |
| WO | WO 2004/032987 | 4/2004 |
| WO | WO 2004/060428 | 7/2004 |
| WO | WO 2005/004945 | 1/2005 |

OTHER PUBLICATIONS

Bosiers et al., "Coronary and endovascular applications of the Absorb™ bioresorbable vascular scaffold", Interv. Cardiol. 4(6), pp. 621-631 (2012).

Miller "Abbott's Bioresorbable Stent Shows Durable Results in ABSORB Trial", The Gray Sheet, pp. 17-18, Mar. 2003.

"Copolymer", Definition and More from the Free Miriam-Webster Dictionary, http://www.merriam-webster.com/dictionary/copolymer, printed, Oct. 29, 2012, 1 pg.

"Copolymer", Definition of Copolymer by the Free Online Dictionary, Thesaurus and Encyclopedia, http://www.thefreedictionary.com/copolymer, printed Oct. 29, 2012, 1 pg.

"Copolymer," Wikipedia: The Free Encyclopedia, http://en.wikipedia.org/wiki/Copolymer, printed Oct. 29, 2012, 5 pgs.

"Copolymer/Define Copolymer at Dictionary.com," and "Copolymer," Encyclopedia Britannica Online, http://dictionary.reference.com/browse/copolymer, printed Oct. 30, 2012, 2 pgs.

"Poly(vinylidene fluoride-co-hexafluoropropylene)", SIGMA-ALDRICH catalog, product detail, downloaded from:www.sigmaaldrich.com/catalog?ProductDetail.do?, Jul. 3, 2010, 2 pgs.

Anonymous "Amorphous Polymers and the Glass Transition Temperature", http://www.irc.leeds.ac.uk/iaps/mod1/node6 html printed Mar. 21, 2003 (3 pages).

Anonymous "A Simple Approach for Glass Transition Temperature Prediction", http://www.geocities.com/ResearchTriangle/Thinktank/4146/6400glass-temperature.html, printed May 5, 2005 (2 pages).

Anonymous, Appendix I—Glass Transition Temperature ($T_g$) www.Dymax.com/pdf/SPIE-Paper-Apendix.pdf, printed May 9, 2005 (2 pages).

Anonymous, "Cardiologists Draw—Up The Dream Stent", Clinica 710:15 (Jun. 17, 1996), http://www.dialogweb.com/cgi/document?req=1061848202959, printed Aug. 25, 2003 (2 pages).

Anonymous, "Differential Scanning Calorimetry", http://www.pslc.ws/macrog/dsc.htm, printed Sep. 29, 2003 (8 pages).

Anonymous, "Glass transition temperature", http://palimpsest.stanford.edu/don/dt/dt1549.html, printed Mar. 21, 2003 (1 page).

Anonymous, "Glass Transition Temperature", http://islnotes.cps.msu.edu/trp/back/mol glas.html, printed May 5, 2005 (1 page).

Anonymous, "How Big are Polymers?", www.chemeng.ucla.edu/che112/Notes, printed May 9, 2005 (13 pages).

Anonymous, "Measuring and Understanding Tg (Glass Transition Temperature)," Arlon, Application Notes (4 pages).

Anonymous, "The Glass Transition", http://www.pslc.ws/macrog/tg.htm, printed Mar. 21, 2003 (11 pages).

Anonymous, "Thermal Properties—Crystallization" (16 pages).

Anonymous, "Thermoplastics—An Introduction", http://www.azom.com/details.asp?ArticleID+83&head=Thermoplastics%2B-%2BAn%2BIntroduction, printed May 18, 2005 (5 pages).

Arvanitoyannis et al., "Novel star-shaped polylactide with glycerol using stannous octoate or tetraphenyl tin as catalyst: 1 Synthesis, characterization and study of their biodegradability", Polymer vol. 36, No. 15, pp. 2947-2956 (1995).

Baird et al, "Dielectric behaviour and morphology of polyvinylidene fluoride", Journal of Material Science 10:1248-1251 (1975).

Birmingham Polymers, Inc., Biodegradation Information, www.absorbables.com (2 pages).

Birmingham Polymers, Inc., Chemical & Physical Properties of Selected Polymers, www.absorbables.com printed Apr. 2, 2015 (2 pages).

Birmingham Polymers, Inc., Inherent Viscosity, www.absorbables.com.

Black et al., "Glass Transitions of Some Block Copolymers", Journal of Applied Polymer Science 18:2307-2310 (1974).

Bliznyuk et al., "Surface Glass Transition Temperature of Amorphous Polystyrene Measured By SFM", pp. 1-5.

Bloembergen et al., "Studies of Composition and Crystallinity of Bacterial Poly(β-hydroxybutyrate-co-β-hydroxyvalerate)", Macromolecules 19, pp. 2865-2871 (1986).

Buchholz et al., "Cooling rate dependence of the glass transition temperature of polymer melts: Molecular dynamics study", Journal of Chemical Physics 117(15):7364-7372 (Oct. 15, 2002).

(56) References Cited

OTHER PUBLICATIONS

Claude Tournut Chapter 31, "Thermoplastic Copolymers of Vinylidene Fluoride," John Scheirs, ed. *Modern Fluoropolymers*, pp. 577-596 (1997), Chichester, England, John Wiley & Sons Ltd.
Translation of a Notification of Reasons for Refusal issued by JPO on Nov. 17, 2009, in connection with Appl. No. 2003-579899, 8 pgs.
Degertekin et al., "Persistent Inhibition of Neointimal Hyperplasia After Sirolimus-Eluting Stent Implantation: Long-Term Clinical, Angiographic, and Intravascular Ultrasound Follow-Up", Circulation 106, pp. 1610-1613 (2002).
Ding et al., "Novel Synthesis of Poly(p-phenylene sulfide) from Cyclic Disulfide Oligomers", Macromolecules 29:4811-4812 (1996).
Eling et al., "Biodegradable materials of poly(L-lactic acid): 1. melt-spun and solution-spun fibres", Polymer, vol. 23, pp. 1587-1593 (1982).
Encyclopedia of Polymer Science and Technology Suppl., 2 Ed. Bikales, 9 title pages (1977).
Fernandez-Martin et al., "Glass Transition Temperature and Heat Capacity of Heterotacticlike PMMA", Journal of Polymer Science: Polymer Physics Edition 19:1353-1363 (1981).
Forrest et al., "Brillouin Light Scattering Determination of the Glass Transition in Thin, Freely-Standing Poly (styrene) Films", Met. Res. Soc. Symp. Proc. vol. 407, pp. 131-136 (1996).
Forrest et al., "Effect of Free Surfaces on the Glass Transition Temperature of Thin Polymer Films", Physical Review Letters 77(10):2002-2005 (Sep. 2, 1996).
Fried, Polymer Science and Technology, Prentice Hall, Englewood Cliffs, New Jersey, 1995, p. 10.
Fryer et al., "Dependence of the Glass Transition Temperature of Polymer Films on Interfacial Energy and Thickness", Macromolecules 34(16):5627-5634 (2001).
Fujii et al., "Investigation of the Stereoregularity of Poly(vinyl Alcohol)", Journal of Polymer Science: Part A 2:2327-2347 (1964).
Gee et al., "The effect of ionizing radiation on the thermal properties of linear high polymers": Part 2. Nylon-6, pp. 192-197 (1970).
Grohens et al., "Tacticity and surface chemistry effects on the glass transition temperature of thin supported PMMA films", Mat. Res. Soc. Symp. 629:FF1.7.1-FF1.7.7 (2000).
Helmenstine, Anne Marie, "Copolymer—Definition of Copolymer," About.com Guide, http://chemistry.about.com/od/chemsitryglossary/g/Copolymer-Definition.htm, printed Oct. 29, 2012, 1 page.
Inoue et al., "An AB block copolymer of oligo(methyl methacrylate) and poly(acrylic acid) for micellar delivery of hydrophobic drugs", Journal of Controlled Release 51:221-229 (1998).
International Search Report for PCT/US2005/018579 filed May 26, 2006, mailed May 24, 2006, 6 pages.
Jacobsen et al.,"Filling of Poly(Lactic Acid) With Native Starch", Polymer Engineering and Science, vol. 36, No. 22, pp. 2799-2804 (1996).
Jaeger et al., "Two-Year Angiographic and Intravascular Ultrasound Follow-Up After Implantation of Sirolimus-Eluting Stents in Human Coronary Arteries", Circulation 107, pp. 381-383 (2003).
Kumar et al., "Biodegradable block copolymers", Advance Drug Delivery Rev. vol. 53, pp. 23-44 (2001).
*KYNAR*® and *KYNAR*®FLEX PVDF, The Base Resins for Demanding Industrial Applications, http.//www.products.arkemagroup.com/print.cfm, printed May 18, 2005 (3 pages).
Lam et al., "Biodegradation of porous versus non-porous poly(L-lactic acid) films", J. of Materials Science: Materials Medicine 5, pp. 181-189 (1994).
Löfgren et al., "Synthesis and Characterization of Biodegradable Homopolymers and Block Copolymers Based on 1,5-Dioxepan-2-one", Macromolecules 27:5556-5562 (1994).
Lotz, Phase Transitions and Structure of Crystalline Polymers, pp. 1-27.
Micoulaut et al., "Glass Transition temperature variation, cross-linking and structure in network glasses: A stochastic approach", Europhysics Letters 47(5):568-574 (1999).
Migliaresi et al., "Dynamic Mechanical and Calorimetric Analysis of Compression-Molded PLLA of Different Molecular Weights: Effect of Thermal Treatments", J. of Applied Polymer Science, vol. 43, pp. 83-95 (1991).
Neuhaus et al., "mTOR Inhibitors: An Overview", Liver Transpl. vol. 7. No. 6, pp. 473-484.
Nijenhuis et al., "Highly crystalline as-polymerized poly(L-lactide)", Polymer bulletin 26, pp. 71-77 (1991).
Parravicini et al., "Crystallization of Poly(Ethylene Terephthalate) (PET) from the Oriented Mesomorphic Form", pp. 875-885 (1994).
Polymer Data Handbook, Oxford Univ. Press. pp. 114-117 (1999).
Property data in Registry on STN 9011-17-0, 6 pgs.
Reeve et al., "Polylactide Stereochemistry:Effect on Enzymatic Degradability", Macromolecules 27, pp. 825-831 (1994).
Rodriguez, Ferdinand, Principles of Polymer Systems, Fourth Edition, Taylor & Francis, Washingon, D.C., 1996, p. 129.
Rogers et al., "Glass Formation in Polymers. I. The Glass Transitions of the Poly-(n-Alkyl Methacrylates)", 61:985-990 (Jul. 1957).
Sarasua et al., "Crystallization and Melting Behavior of Polylactides", Macromolecules 31, pp. 3895-3905 (1998).
Schwartz et al., "Restenosis After Ballon Angioplasty", Circulation vol. 82, No. 6, pp. 2190-2200 (1990).
Schwartz et al., "Restenosis and the Proportional Neointimal Response to Coronary Artery Injury: Results in a Porcine Model", JACC vol. 19, No. 2, pp. 267-74 (1992).
Scott et al., "Ehtylene-Vinyl Acetate Semi-Batch Emulsion Copolymerization: Use of Factorial Experiments for Process Optimization", pp. 539-555 (1993).
Sichina, "Characterization of Polymers by TMA", Perkin Elmer Polymers technical note (9 pages).
Sousa et al., "Lack of Neointimal Proliferation After Implantation of Sirolimus-Coated Stents in Human Coronary Arteries: A Quantitative Coronary Angiography and Three-Dimensional Intravascular Ultrasound Study", Circulation 103, pp. 192-195 (2001).
Sousa et al., "Two-Year Angiographic and Intravascular Ultrasound Follow-Up After Implantation of Sirolimus-Eluting Stents in Human Coronary Arteries", Circulation 107, pp. 381-383 (2003).
Sperling, Introduction to Physical Polymer Science, 3rd Ed. 21 title pages (2001).
Sun et al., "Novel Copolyesters Containing Naphthalene Structure. I. From Bis(hydroxyalkyl)naphthalate and Bis[4-(2-hydroxyethoxy)aryl] Compounds", Journal of Polymer Science: Part A: Polymer Chemistry 34:1783-1792 (1996).
Taylor et al., "An Applied Approach to Film Formation; The glass transition temperature evolution of plasticized latex films", downloaded May 5, 2005 (13 pages).
Techspray Product Information, HFE Flux Remover, http://www.techsoray.com/1686info.htm, printed May 9, 2005 (2 pages).
Tokoh et al., "Glass Transition Temperature of Ethylene-Vinyl Alcohol Copolymers", Chemistry Express vol. 2, No. 9, pp. 575-578 (1987).
Translation of a Notification of Reasons for Refusal issued by JPO on Nov. 17, 2009, in connection with Appl. No. 2003-579899, 3 pgs.
Translation of a Notification of Refusal issued by JPO on Oct. 4, 2011, in connection with Appl. No. 2006-517163, 7 pgs.
Translation of Notification of Refusal received from JPO for Appl. No. 2007-515347, mailed Jul. 10, 2012, 8 pgs.
*Transplant* 2001: Certican (Everolimus) Effective in Preventing Acute Rejection in Renal Transplantation, http://www.docouide.com/do.nsf/PrintPrint/A9A24F321A71712485256A4E00689824, printed May 9, 2005 (2 pages).
Tsige et al., "Simulation study of the glass transition temperature in poly(methyl methacrylate)", Physical Review E vol. 65: (2002) (8 pages).
van Beusekom et al., "Coronary stent coatings", Coronary Artery Disease 5(7): 590-596 (Jul. 1994).
Van de Velde et al., "Biopolymers: overview of several properties and consequences on their applications", Polymer Testing vol. 21, pp. 433-442 (2002).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

(56) References Cited

OTHER PUBLICATIONS

Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology,* Clinica 720:22 (Sep. 2, 1996), http://www.dialogweb.com/cgi/document?reg=1061848017752, printed Aug. 25, 2003 (2 pages).
Aoyagi et al., *Preparation of cross-linked aliphatic polyester and application to thermo-responsive material,* Journal of Controlled Release 32:87-96 (1994).
Barath et al., *Low Dose of Antitumor Agents Prevents Smooth Muscle Cell Proliferation After Endothelial Injury,* JACC 13(2): 252A (Abstract) (Feb. 1989).
Barbucci et al., *Coating of commercially available materials with a new heparinizable material,* J. Biomed. Mater. Res. 25:1259-1274 (Oct. 1991).
Chung et al., *Inner core segment design for drug delivery control of thermo-responsive polymeric micelles,* Journal of Controlled Release 65:93-103 (2000).
Dev et al., *Kinetics of Drug Delivery to the Arterial Wall Via Polyurethane-Coated Removable Nitinol Stent: Comparative Study of Two Drugs,* Catheterization and Cardiovascular Diagnosis 34:272-278 (1995).
Dichek et al., *Seeding of Intravascular Stents with Genetically Engineered Endothelial Cells,* Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin,* JACC, 4A (701-1), Abstract (Feb. 1994).
Helmus, *Overview of Biomedical Materials,* MRS Bulletin, pp. 33-38 (Sep. 1991).
Herdeg et al., *Antiproliferative Stent Coatings: Taxol and Related Compounds,* Semin. Intervent. Cardiol. 3:197-199 (1998).
Huang et al.,*Biodegradable Polymers Derived from Aminoacids,* Macromol. Symp. 144, 7-32 (1999).
Inoue et al., *An AB block copolymer of oligo(methyl methacrylate) and poly(acrylic acid) for micellar delivery of hydrophobic drugs,* Journal of Controlled Release 51:221-229 (1998).
Kataoka et al., *Block copolymer micelles as vehicles for drug delivery,* Journal of Controlled Release 24:119-132 (1993).
Katsarava et al., *Amino Acid-Based Bioanalogous Polymers. Synthesis and Study of Regular Poly(ester amide)s Based on Bis(α-amino acid)α, ω-Alkylene Diesters, and Aliphatic Dicarbolic Acids,* Journal of Polymer Science, Part A: Polymer Chemistry, 37(4), 391-407 (1999).
Lambert et al., *Localized Arterial Wall Drug Delivery From a Polymer-Coated Removable Metallic Stent,* Circulation 90(2):1003-1011 (Aug. 1994).
Levy et al., *Strategies for Treating Arterial Restenosis Using Polymeric Controlled Release Implants,* Biotechnol. Bioact. Polym. [Proc. Am. Chem. Soc. Symp.], pp. 259-268 (1994).
Liu et al., *Drug release characteristics of unimolecular polymeric micelles,* Journal of Controlled Release 68:167-174 (2000).
Marconi et al., *Covalent bonding of heparin to a vinyl copolymer for biomedical applications,* Biomaterials 18(12):885-890 (1997).
Matsumaru et al., *Embolic Materials for Endovascular Treatment of Cerebral Lesions,* J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice,* Chem. Pharm. Bull. 33(6) 2490-2498 (1985).
Miyazawa et al., *Effects of Pemirolast and Tranilast on Intimal Thickening After Arterial Injury in the Rat,* J. Cardiovasc. Pharmacol., pp. 157-162 (1997).
Nordrehaug et al.,*A novel biocompatible coating applied to coronary stents,* EPO Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty,* American Heart Journal 136(6):1081-1087 (Dec. 1998).
Ozaki et al., *New Stent Technologies,* Progress in Cardiovascular Diseases, vol. XXXIX(2):129-140 (Sep./Oct. 1996).
Perchar et al., *Poly(ethylene glycol) Multiblock Copolymer as a Carrier of Anti-Cancer Drug Doxorubicin,* Bioconjucate Chemistry 11(2):131-139 (Mar./Apr. 2000).
Peng et al., *Role of polymers in improving the results of stenting in coronary arteries,* Biomaterials 17:685-694 (1996).
Saotome, et al., *Novel Enzymatically Degradable Polymers Comprising α-Amino Acid, 1,2-Ethanediol, and Adipic Acid,* Chemistry Letters, pp. 21-24, (1991).
De Scheerder et al., *Biocompatibility of Polymer-Coated Oversized Metallic Stents Implanted in Normal Porcine Coronary Arteries, Atherosclerosis* 114:105-114 (1995).
Shigeno, *Prevention of Cerebrovascular Spasm By Bosentan, Novel Endothelin Receptor,* Chemical Abstract 125:212307 (1996).
van Beusekom et al., *Coronary stent coatings, Coronary Artery Disease* 5(7):590-596 (Jul. 1994).
Wilensky et al., *Methods and Devices for Local Drug Delivery in Coronary and Peripheral Arteries,* Trends Cardiovasc. Med. 3(5):163-170 (1993).
Yokoyama et al., *Characterization of physical entrapment and chemical conjugation of adriamycin in polymeric micelles and their design for in vivo delivery to a solid tumor,* Journal of Controlled Release 50:79-92 (1998).
International Search Report and Written Opinion for PCT/US2004/040121, filed Nov. 30, 2004, mailed Apr. 12, 2005, 12 pgs.
EPO Examination Report for application 04 812 597.5-2307, mailed Feb. 26, 2007, 2 pgs.
EPO Examination Report for application 04 812 597.5-2307, mailed Sep. 6, 2007, 3 pgs.
EPO Examination Report for application 04 812 597.5-2307, mailed Jul. 4, 2008, 3 pgs.
International Search Report and Written Opinion for PCT/US2004/017060, mailed Dec. 30, 2004, 10 pgs.
International Search Report for 05780079.9-2107, mailed Jan. 17, 2008, 6 pages.
Perego et al., "Copolymers of L and D, L Lactide with 6-caprolactone:synthesis and characterization", Macromol. Chem. 194, pp. 2463-2469 (1993).

* cited by examiner

TEMPERATURE CONTROLLED CRIMPING

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is a continuation-in-part of U.S. patent application Ser. No. 10/725,698, filed on Dec. 1, 2003, the entire disclosure of which is incorporated by reference.

BACKGROUND

Percutaneous transluminal coronary angioplasty (PTCA) is a procedure for treating heart disease. A surgeon introduces a catheter assembly having a balloon portion percutaneously into the cardiovascular system of a patient via the brachial or femoral artery. The surgeon advances the catheter assembly through the coronary vasculature until the balloon portion crosses the occlusive lesion. Once in position, the surgeon inflates the balloon to radially compress the atherosclerotic plaque of the lesion and remodel the vessel wall. The surgeon then deflates the balloon to remove the catheter.

An advance on PTCA involved using an intravascular stent. Mechanically, stents act as scaffoldings, physically holding open and, if desired, expanding the vessel wall. Typically, stents compress for insertion through small vessels and then expand to a larger diameter once in position. U.S. Pat. No. 4,733,665, issued to Palmaz; U.S. Pat. No. 4,800,882, issued to Gianturco; and U.S. Pat. No. 4,886,062, issued to Wiktor disclose examples of PTCA stents.

Before this procedure can occur, equipment for the procedure must be manufactured. Stent crimping is a critical step in manufacturing this equipment in that stent retention depends on it. Generally, stent crimping is the act of affixing the stent to the delivery catheter or delivery balloon so that it remains affixed to the catheter or balloon until the physician desires to deliver the stent at the treatment site. Current stent crimping technology is sophisticated. A short time ago, one process used a roll crimper. This damaged many polymer coatings due to its inherent shearing action. Next came the collet crimper; in it, metal jaws are mounted into what is essentially a drill chuck. The jaws move in a purely radial direction. This movement was not expected to shear the coating, because it applied forces only normal to the stent surface. But some stent geometries require that stent struts scissor together during crimping. In those geometries, even if the crimper imposes only normal forces, the scissor action of the stent struts imparts shear. Finally, the iris or sliding-wedge crimper imparts mostly normal forces with some amount of tangential shear.

To use a roll crimper, first the stent is slid loosely onto the balloon portion of the catheter. This assembly is placed between the plates of the roll crimper. With an automated roll crimper, the plates come together and apply a specified amount of force. They then move back and forth a set distance in a direction that is perpendicular to the catheter. The catheter rolls back and forth under this motion, and the diameter of the stent is reduced. The process can be broken down into more than one step, each with its own level of force, translational distance, and number of cycles. With regard to a stent with a drug eluting coating, this process imparts a great deal of shear to the stent in a direction perpendicular to the catheter or catheter wall. Furthermore, as the stent is crimped, there is additional relative motion between the stent surface and the crimping plates. As a result, this crimping process tends to damage the drug eluting stent coating.

The collet crimper is equally conceptually simple. A standard drill-chuck collet is equipped with several pie-piece-shaped jaws. These jaws move in a radial direction as an outer ring is turned. To use this crimper, a stent is loosely placed onto the balloon portion of a catheter and inserted in the center space between the jaws. Turning the outer ring causes the jaws to move inward. An issue with this device is determining or designing the crimping endpoint. One scheme is to engineer the jaws so that when they completely close, they touch and a center hole of a known diameter remains. Using this approach, turning the collet onto the collet stops crimps the stent to the known outer diameter. While this seems ideal, it can lead to problems. Stent struts have a tolerance on their thickness. Additionally, the process of folding noncompliant balloons is not exactly reproducible. Consequently, the collet crimper exerts a different amount of force on each stent in order to achieve the same final dimension. Unless this force, and the final crimped diameter, is carefully chosen, the variability of the stent and balloon dimensions can yield stent coating or balloon damage.

Furthermore, although the collet jaws move in a radial direction, they move closer together as they crimp. This action, combined with the scissoring motion of the struts, imparts tangential shear on the coatings that can also lead to damage. Lastly, the actual contact surfaces of the collet crimper are the jaw tips. These surfaces are quite small, and only form a cylindrical surface at the final point of crimping. Before that point, the load being applied to the stent surface is discontinuous.

In the sliding wedge or iris crimper, adjacent pie-piece-shaped sections move inward and twist, much like the leaves in a camera aperture. This crimper can be engineered to have two different types of endpoints. It can stop at a final diameter, or it can apply a fixed force and allow the final diameter to float. From the discussion on the collet crimper, there are advantages in applying a fixed level of force as variabilities in strut and balloon dimension will not change the crimping force. The sliding wedges impart primarily normal forces, which are the least damaging to stent coatings. As the wedges slide over each other, they impart some tangential force. But the shear damage is frequently equal to or less than that of the collet crimper. Lastly, the sliding wedge crimper presents a nearly cylindrical inner surface to the stent, even as it crimps. This means the crimping loads are distributed over the entire outer surface of the stent.

All current stent crimping methods were developed for all-metal stents. Stent metals, such as stainless steel, are durable and can take abuse. When crimping was too severe, it usually damaged the underlying balloon, not the stent. But polymeric coatings present different challenges.

Moreover, as part of polymeric stent manufacture, brittle polymeric material is laser cut. The polymer's brittle nature and the stress induced by laser cutting often causes stress cracking in the polymeric stent.

In the drug eluting stent arena, drugs are commonly placed on the stent in combination with a polymer or mixed into the polymer for polymeric stents. This placement typically coats all stent surfaces or causes the drug to be distributed throughout the polymeric stent. Then the stent is crimped onto the catheter. In general, polymer coatings are softer, weaker, and less durable than the underlying stent material. Upon crimping with a sliding wedge crimper, and following crimp protocols for the particular stent, coating damage is frequently seen. FIGS. 1 and 2 show an Elasteon 80A (a polyurethane) coating on poly(ethylene-co-vinyl alcohol) (EVAL) after crimp, grip, and the wet expansion test.

Grip is a process conducted after crimping to further increase stent retention. An outer sleeve restrains the crimped stent. Simultaneously, pressure and heat are applied to the stent-balloon section. Under this action, the balloon material deforms slightly, moving in between the struts. In a wet expansion test, the final stent-on-catheter assembly is immersed in deionized water at 37° C. for 30 seconds. Then the balloon is inflated according to the device instructions to at least a nominal pressure (8 atmospheres). After holding this pressure for 30 seconds, the balloon is deflated, and the stent slides off. After drying, the stent can be examined by optical microscopy or scanning electron microscopy for coating damage.

The primary purpose of the polymer in the stent coating is to contain the drug and control its release at a desired rate. Other obvious specifications for the polymer are a high level of vascular biocompatibility and the ability to flex and elongate to accommodate stent expansion without cracking or peeling. Meeting all of these objectives, while also possessing a high level of toughness and strength to withstand conventional crimping process, can be challenging.

A crimping process that minimizes damage to the polymer coatings of stents is needed. Moreover, a crimping process that minimizes internal stress or strain in the polymeric substrate of a polymeric stent is also needed.

SUMMARY

The current invention comprises several embodiments, some of which relate to extracorporeal methods of making medical devices or implantable medical devices. These devices can comprise portions with coatings. In some embodiments, the coating comprises a polymer or polymer combination or drug(s). The piece comprising the coating is crimped onto another part of the device or onto a separate device. In some embodiments, crimping is done at non-ambient temperatures. Sometimes non-ambient-temperature crimping comprises changing the temperatures of the coating, the piece comprising the coating, the medical device, the crimping device, or any combination of these. Likewise, medical devices made using these methods and devices for implementing these methods are also part of this invention. In some embodiments the medical device is or comprise a stent.

Specific heating and cooling profiles are used in different invention embodiments. For instance, embodiments of crimping methods include adjusting the temperature of the coating to a target temperature followed by a crimping step; adjusting the temperature of the coating to a target temperature during a crimping step; adjusting the temperature of the coating to a target temperature and maintaining the temperature of the coating within plus or minus 5° C. of the target temperature during a crimping step; adjusting the temperature of the coating to a target temperature followed by crimping such that the temperature of the coating remains within plus or minus 10° C. of the target temperature during a crimping step; and adjusting the temperature of the coating to a temperature other than ambient towards a target temperature and continuing to adjust the temperature of the coating towards the target temperature during a crimping step. Alternatively, the temperature of the coating can first be adjusted to a target temperature with the crimper jaws then closing. After that, the temperature can be adjusted to a second temperature, followed by opening the crimper jaws.

Embodiments in which the target temperature takes values based on Tg and intervals around Tg are described, with the goal of some embodiments being to simultaneously minimize deformation- and delamination-based failure during crimping. In some embodiments, the target temperature ultimately depends on the predominate failure mode of the polymer coating, Tg of the coating, shore D hardness of the polymer coating at ambient temperature, and shore hardness of the polymer coating at the target temperature, among other factors.

In some embodiments, invention methods relate to making medical devices comprising at least one piece wherein the piece can comprise a polymer or polymer combination. In some embodiments, the piece comprises a polymer or polymer combination and drug(s). A typical method comprises choosing a target temperature based on the mechanical behavior of the polymeric material, sometimes the behavior during crimping. The method further comprises juxtaposing the closing of the crimping jaws with adjusting the temperature of the piece in any combination. For instance, the following heating regimes are practical:

- adjusting the temperature of the piece to a target temperature followed by a crimping step;
- adjusting the temperature of the piece to a target temperature during a crimping step;
- adjusting the temperature of the piece to a target temperature and maintaining that temperature within plus or minus 5° C. of the target temperature during a crimping step;
- adjusting the temperature of the piece to a target temperature followed by crimping such that the temperature of the piece remains within plus or minus 10° C. of the target temperature during the crimping step; and
- adjusting the temperature of the piece to a temperature other than ambient towards a target temperature and continuing to adjust the temperature of the piece towards the target temperature during a crimping step.

Any of these regimes can optionally be coupled with continued heating for a time after crimping—either while crimping pressure is applied or after pressure is removed.

In these embodiments or others the heating regime can comprise closing the crimper, adjusting the temperature of the piece to a second temperature, and opening the crimper wherein the second temperature is greater than or less than the target temperature. Some medical devices further comprise a catheter. In those devices, the crimping step of invention methods can be used to attach the piece to the catheter.

Invention methods can be used on a variety of polymeric materials including those characterized as having Tg above ambient temperature. In some embodiments the methods act on polymeric materials comprising ABS resins; acrylic polymers and acrylic copolymers; acrylonitrile-styrene copolymers; alkyd resins; biomolecules; cellulose ethers; celluloses; copoly(ether-esters); copolymers of polycarboxylic acids and poly-hydroxycarboxylic acids; copolymers of vinyl monomers with each other and olefins; cyanoacrylates; epoxy resins; ethylene vinyl alcohol copolymers; ethylene-methyl methacrylate copolymers; ethylene-vinyl acetate copolymers; ethylene-α-olefin copolymers; poly(amino acids); poly (anhydrides); poly(butyl methacrylates); poly(ester amides); poly(ester-urethanes); poly(ether-urethanes); poly(imino carbonates); poly(orthoesters); poly(silicone-urethanes); poly(tyrosine arylates); poly(tyrosine-derived carbonates); polyacrylates; polyacrylic acid; polyacrylic acids; polyacrylonitrile; polyacrylonitrile; polyalkylene oxalates; polyamides; polyamino acids; polyanhydrides; polycarbonates;

polyearboxylic acids; polycyanoacrylates; polyesters; polyethers; poly-hydroxycarboxylic acids; polyimides; polyisobutylene and ethylene-α-olefin copolymers; polyketones; polymethacrylates; polyolefins; polyorthoesters; polyoxymethylenes; polyphosphazenes; polyphosphoesters; polyphosphoester urethanes; polyphosphoesters; polyphosphoester-surethane; polyurethanes; polyvinyl aromatics; polyvinyl esters; polyvinyl ethers; polyvinyl ketones; polyvinylidene halides; silicones; starches; vinyl copolymers vinyl-olefin copolymers; and vinyl halide polymers and copolymers. Some embodiments select the group of polymers to specifically exclude any one of or any combination of the polymers listed above.

Specific examples of useful polymers for some embodiments include the following polymers: starch, sodium alginate, rayon-triacetate, rayon, polyvinylidene fluoride, polyvinylidene chloride, polyvinyl pyrrolidone, polyvinyl methyl ether, polyvinyl chloride, polyvinyl acetate, polystyrene, polyisocyanate, polyisobutylene, polyethylene glycol, polydioxanone, polycaprolactone, polycaprolactam, KYNAR (brand poly(vinylidene fluoride) available from Atofina), polyacrylonitrile, poly(trimethylene carbonate), poly(L-lactic acid), poly(lactide-co-glycolide), poly(hydroxyvalerate), poly(hydroxybutyrate-co-valerate), poly(hydroxybutyrate-co-hydroxyvalerate), poly(hydroxybutyrate), poly(glycolide), poly(glycolic acid), poly(D,L-lactide-co-L-lactide), poly(D,L-lactide-co-glycolide), poly(D,L-lactide), poly(4-hydroxybutyrate), poly(3-hydroxybutyrate), poly(3-hydroxy valerate), Nylon 66, hyaluronic acid, fibrinogen, fibrin, elastin-collagen, collagen, cellulose propionate, cellulose nitrate, cellulose butyrate, cellulose acetate butyrate, cellulose acetate, cellulose, cellophane, carboxymethyl cellulose, or poly(2-hydroxyethyl methacrylate), Chitin, Chitosan, EVAL, poly(butyl methacrylate), poly(D,L-lactic acid), poly(D,L-lactide), poly(glycolic acid-co-trimethylene carbonate), poly (hydroxybutyrate-co-valerate), poly(hydroxyvalerate), poly (iminocarbonate), poly(lactide-co-glycolide), poly(L-lactic acid), poly(N-acetylglucosamine), poly(trimethylene carbonate), poly(vinyl chloride), poly(vinyl fluoride), poly(vinylidene chloride), poly(vinylidene fluoride), poly(vinylidene fluoride-co-chlorotrifluoroethylene), poly (vinylidene fluoride-co-hexafluoropropene), polyanhydride, polyorthoester, polyurethane, polyvinyl alcohol, polyvinyl chloride, rayon, SOLEF 21508 (formulation available from Solvay Solexis), and PEO/PLA. Some embodiments select the group of polymers to specifically exclude any one of or any combination of the polymers listed above.

Some invention methods operate on drug-containing pieces. In some of these embodiments, the drugs are selected from the following types: antiproliferative, antineoplastic, antiinflammatory, antiplatelet, anticoagulant, antifibrin, antithrombin, antimitotic, antibiotic, antioxidants, or their combinations.

The target temperature can be chosen in a number of ways. For instance, the target temperature can be

- within or above the range defined by definition 1, definition 2, definition 3, definition 4, definition 5, definition 6, or definition 7 of the Tg range of the polymer or polymer combination;
- above ambient temperature;
- above room temperature;
- between ambient temperature and upper Tg of the Tg range;
- between ambient temperature and lower Tg of the Tg range;
- between −40° C. and upper Tg of the Tg range;
- between −40° C. and lower Tg of the Tg range;
- between −40° C. and ambient temperature;
- at or above 60° C.;
- between 60° C. and upper Tg of the Tg range;
- between 60° C. and lower Tg of the Tg range; or
- between 60° C. and ambient temperature.

Some invention embodiments choose the target temperature to avoid ambient temperature or a window around ambient temperature. Other embodiments choose the target temperature such that therapeutic agents present in the coating avoid substantial decomposition.

In some embodiments, target temperature is selected from a group that specifically excludes any one or any combination of the temperature range is described above.

Some invention embodiments choose the target temperature to simultaneously minimize deformation- and delamination-based failure during crimping. Some invention embodiments choose the target temperature to yield an improvement in shore hardness.

The annealing temperature can be selected from any of the temperature's described above for the target temperature. Moreover, in some embodiments, annealing temperature is selected from a group that specifically excludes any one or any combination of the temperature ranges described above.

Different invention embodiments use a variety of methods for achieving the temperature adjustment of the polymeric material. For instance, the following ways of changing the temperature are all within the scope of the current invention:

- contacting the polymeric material or piece with a heat source.
- directing a heated gas at the polymeric material or piece;
- placing the polymeric material or piece near a heated surface for emitting thermal or infrared radiation to the coating or coated piece;
- placing the polymeric material or polymeric material or piece near a heated surface to enable convection to the coating or coated piece from the surface;
- heating the jaws of the crimper and thermally contacting the polymeric material or piece with the crimper jaws;
- for crimper jaws that allow the passage of infrared radiation, bathing the stent on catheter with infrared radiation;
- heating the stent on catheter in an incubator or oven to pre-equilibrate the stent on catheter to the desired temperature before crimping.

For some invention devices useful in practicing invention methods, the heat source is integrated with a crimping device. In some embodiments, the piece is selected from self-expandable stents, balloon-expandable stents, and stent-grafts.

DETAILED DESCRIPTION

This document incorporates by this reference the entire disclosure of U.S. patent application Ser. No. 10/725,698, filed on Dec. 1, 2003.

Figure 1:
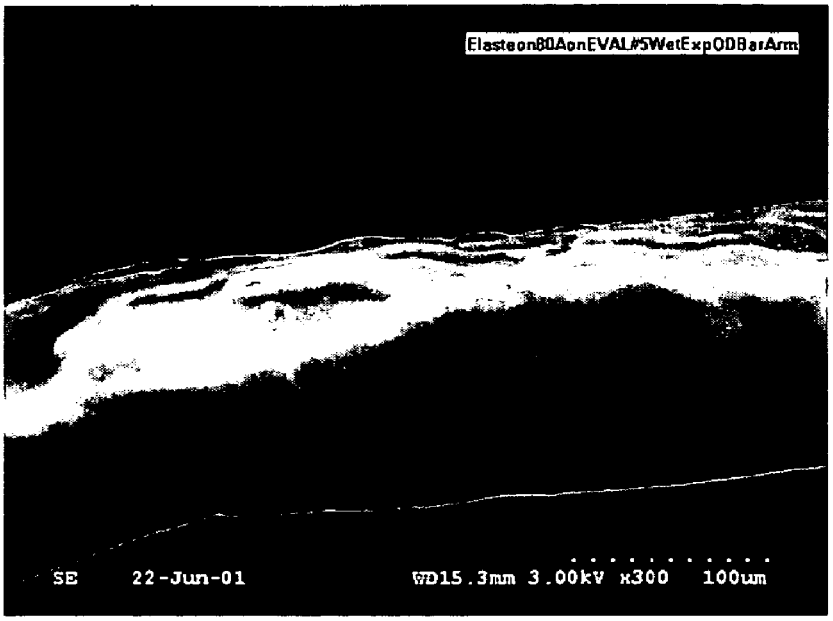
FIG. 1 shows a coating as prepared in Example 1, which is an Elasteon 80A coating on EVAL after crimp, grip, and the wet expansion test.
Figure 2:
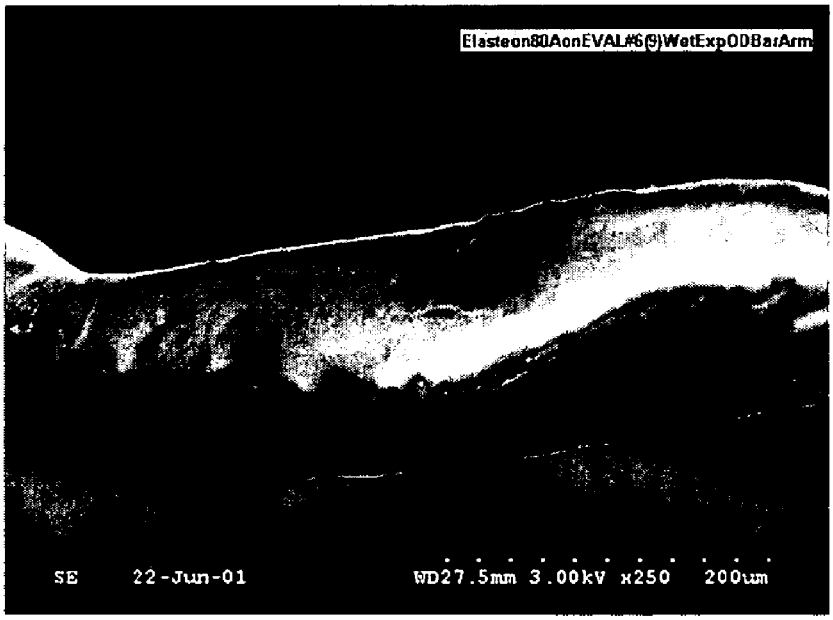
FIG. 2 shows another coating as prepared in Example 1, which is Elasteon 80A coating on EVAL after crimp, grip, and the wet expansion test.
Figure 3:
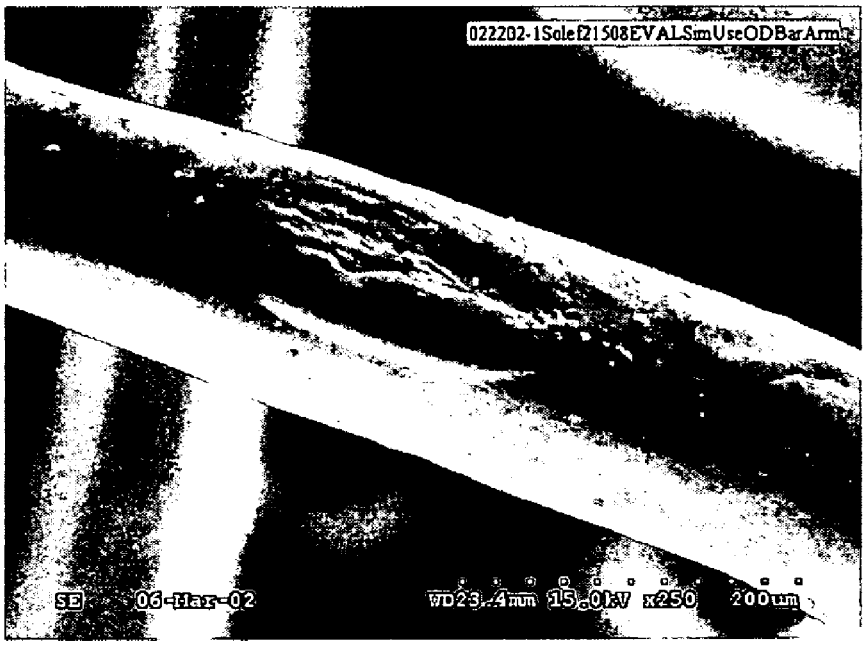
FIG. 3 shows a topcoat of Solef 21508 on EVAL made using the procedures of Example 3.
Figure 4:
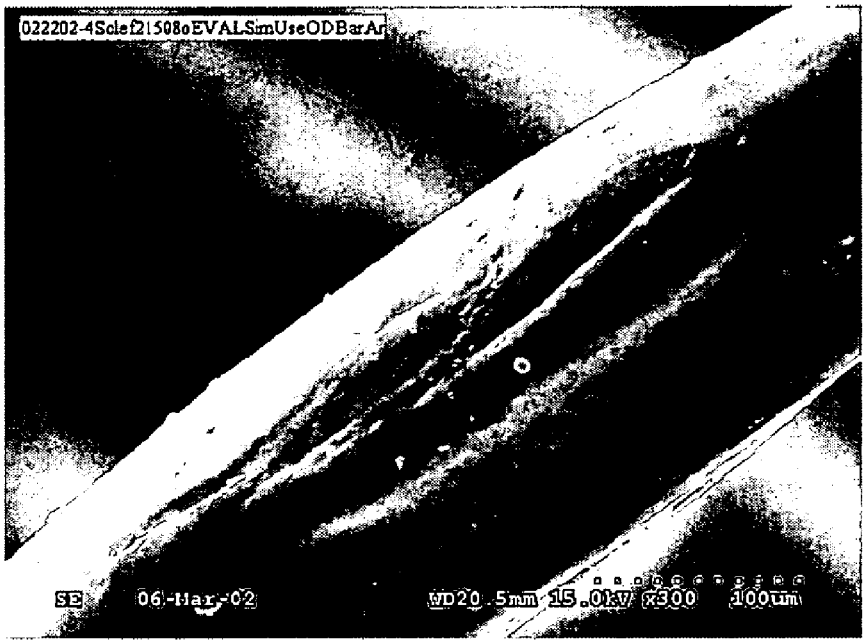
FIG. 4 shows another topcoat of Solef 21508 on EVAL, also made using the procedures of Example 3.

FIGS. 1 and 2 show that the coating on the outer surface of the stent, in one case, has been pinched or wrinkled over, while in the other, has been smeared off. Similarly, FIGS. 3 and 4 show a topcoat of Solef 21508 on EVAL. Solef 21508 is the softest poly(hexafluoropropene-co-vinylidene fluoride) thermoplastic polymer commercially available.

FIGS. 3 and 4 show dents in the high spots of the strut arms. Most high spots of these two stents show similar damage. For these reasons, polymer coatings made of lower durometer (80A for example) polymers frequently fail quality assurance tests. EVAL, a hard plastic, seems to hold up to standard crimping, but it has a hardness of 85 shore D. For comparison, the low-density polyethylene used in milk containers is 47-55 shore D.

Some embodiments of this invention are directed at stents containing a substrate material that is polymeric in nature and methods of manufacturing those stents. Some methods pertain to crimping the stent to the delivery device or balloon.

In some embodiments, crimping is done at a temperature greater than Tg; in some embodiments, crimping is done at a temperature greater than ambient but not necessarily greater than Tg. A device for crimping the polymeric stent onto the delivery device is also contemplated as an invention embodiment. The device can resemble any crimping device as is known in the art or in this document. Additionally, the device is especially modified so that it can heat the stent during crimping. In some embodiments, the device can apply pressure and heat simultaneously. In these or other embodiments, after crimping, the crimping device can hold the stent at an elevated temperature, which may be selected such that it is greater than, equal to, or less than the target temperature or may be selected to specifically exclude temperatures greater than, equal to, or less than the target temperature. In some embodiments, the device crimps the polymeric stent while the stent is heated by other means.

In some embodiments, the crimping method comprises:

placing the stent in the crimping device;

heating the stent to a target temperature long enough that the stent substantially reaches the target temperature;

applying pressure (radial compression pressure) to the stent to attach it to a delivery device;

holding the stent at a radial compression pressure adequate to affix it to the delivery device and holding the stent at an annealing temperature for a time sufficient to set the crimp state into the polymeric stent or coating;

removing the stent-delivery-device combination.

The stent can be heated for up to one hour, 30 seconds to one hour, or for 30 seconds. In some embodiments, the stent is heated long enough that the material becomes ductile enough to adequately lower the brittleness of the stent. Adequate means having a value for the parameter in question such that one of ordinary skill in the art would expect the invention to function in the particular application. For example, "adequately lower the brittleness of the stent" means that the brittleness of the stent is reduced enough to warrant the extra heating step and the extra cost and complication of the heating step, as viewed by one of ordinary skill in the art.

In some embodiments the radial compression pressure is chosen so that no damage to the stent or coating occurs. In some embodiments, the radial compression pressure is chosen so that any damage or deformation that occurs is insufficient to cause one of ordinary skill in the art to reject the stent for use.

In the forgoing embodiments or others, variable temperature means a temperature above ambient. In these or other embodiments, it means a temperature equal to, above or below Tg of the material. In some embodiments, variable temperature means a temperature equal to or below ambient. In some embodiments, the stent is cooled to ambient temperature or below before the radial compression pressure is removed.

In the forgoing embodiments or others, a time sufficient to set the crimp state is any time long enough that the polymeric stent or coating has substantially assumed the new shape induced by crimping such that it substantially retain this shape until the stent is implanted. In these or other embodiments, this time is 1 second to 2 hours, 2 seconds to 1 hour, 3 seconds to 30 minutes, 4 sec to 5 minutes; 1 second to 5 minutes, 2 seconds to 5 minutes, or 3 seconds to 5 minutes.

This procedure is believed to provide the polymer chains with increased mobility and such that they relax into a lower energy (less stressed) configuration. Using this procedure results in polymeric stents with significantly fewer cracks.

In a separate production step, polymeric stents are sometimes sterilized with e-beam radiation. E-beam sterilization frequently exhibits higher polymer degradation rates at high stress regions in the polymer (stent). But after the heat crimping of this invention, which relieves extrusion and laser-cutting-induced stress and strain, e-beam sterilization of treated stents results in significantly fewer cracks and exhibits less pronounced polymer degradation rates at high stress regions in the polymer.

A crimp process in which the coated stent or polymeric stent is held at a target temperature, which may be different from ambient, is disclosed. Temperatures above ambient can be used in cases where the Tg is above ambient or room temperature and greater ductility is desired. For purposes of this disclosure, ambient temperature is the temperature of the crimper or polymer when the crimper or polymer has not been purposely heated or cooled. Typically, this temperature will be close to room temperature or the temperature surrounding the crimping equipment or the polymer. Similarly, for purposes of this disclosure, a target temperature is a temperature numerically different from ambient temperature brought about by purposely heating or cooling the crimper, stent, balloon, polymer, or any combination of these. For purposes of this disclosure, "polymer", "polymer combination" and "polymer mixture" are synonymous, meaning a composition of one polymer or, when more than one polymer, a mixture of, a blend of, a copolymerization of, or any other combination of more than one polymer. The combination can occur after the polymers are polymerized or can occur during the polymerization of monomer into one or more polymers.

| Polymer | Tg ° C. | Durometer Hardness Shore D | Temperature Range for Greater Hardness | Temperature Range for Ductility |
|---|---|---|---|---|
| Solef 21508 | −29 | 60 | −62 to 10 | Ambient to 60 |
| Elasteon 80A | −100, 0 | 30-35 | −110 to −10 | Ambient to 60 |

-continued

| Polymer | Tg ° C. | Durometer Hardness Shore D | Temperature Range for Greater Hardness | Temperature Range for Ductility |
|---|---|---|---|---|
| Elasteon 55D | −100, 0 | 55 | −110 to −10 | Ambient to 60 |
| EVAL-E151 | 55 | 85 | Zero to Ambient | 50 to 100 |
| Kynar-Flex 2800 | −30 | 65-70 | −62 to 10 | Ambient to 60 |
| Butvar B-90 | 72-78 | 85-90 | Zero to Ambient | Ambient to 100 |
| Kynar 710 | −30 | 76-80 | −62 to 10 | Ambient to 60 |
| Poly(n-butyl methacrylate) | 20 | NA | −30 to 15 | Ambient to 60 |

A representative method includes heating a polymer on a medical device to or towards a target temperature. Next, either after the target temperature has been reached or while the polymer is changing temperature towards the target temperature, the portion of the medial device containing the polymer is crimped onto another portion of the medical device or onto another medical device. Crimping is done in a temperature region designed to minimize both cohesive and adhesive failure (or deformation- and delamination-based failure) caused by local pressure from the jaws or surfaces of the crimping device, and deformation of the stent caused by reducing its diameter. For instance, a stent can be heated with a stream of air and crimped onto a delivery catheter with an iris crimper. Moreover, in some embodiments, the temperature region is chosen so that internal stress in the polymeric stent or polymer coating diminishes over time after crimping.

Heating is generically discussed as "adjusting" the temperature of the polymer, the crimper, or the medical device. Adjusting the temperature comprises placing the object that is to have its temperature adjusted into thermal contact with a heat source. For purposes of this disclosure, thermal contact with a heat source means heat source arrangement vis-à-vis the object so that energy would flow or be carried from the heat source to the object. Thermal contact is a generic term at least encompassing an arrangement of the object such that radiation, conduction, or convection from the heat source would transfer energy. In some embodiments, thermal contact is defined to exclude any of radiation, conduction, convection, or any combination of these.

Different invention embodiments employ different heating profiles. For instance, when the heating profile calls for softening the polymer by choosing a target temperature above some temperature value, the polymer is adjusted to the target temperature before crimping and then crimping occurs (with or without some amount of temperature decrease before crimping); alternatively, the polymer is adjusted to the target temperature before crimping and maintained at or near the target temperature during crimping; alternatively, crimping is started, the polymer is adjusted to the target temperature, and crimping is completed. For purposes of this disclosure, "maintained near the target temperature" means that the temperature of the polymer at the instant of contact with the crimper is the target temperature plus or minus 20° C., 15° C., 10° C., 5° C., 2° C. or 1° C. In some embodiments, "maintained near the target temperature" means that the temperature of the polymer at the instant of contact with the crimper is the target temperature plus or minus 10° C.

Polymers on crimped stents or crimped polymeric stents exhibit adhesive and cohesive failure as two main failure modes. In adhesive failure, polymer is sheared off the stent due to poor adhesion to the metal stent or between the polymer molecules in a polymeric stent. This is a failure of the polymer due to poor interaction between polymer molecules. Since at higher temperatures, particularly those above Tg, polymeric materials are softer, a higher temperature crimp process should assist in preventing adhesive failure. Adhesive failure is sometimes referred to as an adhesive-based failure or delamination-based failure. When a polymer exhibits adhesive failure, that polymer becomes a candidate for crimping above Tg of the polymer. Adhesive failure is also caused by a build-up of stress. Heating the polymer above its Tg lowers its modulus and decreases the internal stress within the polymer. When stents are crimped, whether polymer coated or substantially polymeric, certain portions of the stent undergo elongation. If too much elongation occurs, the polymer will crack. The ultimate elongation of polymers depends on the temperature, and heating the polymer above its Tg can increase the ultimate elongation, thereby preventing failure. If the polymer exhibits a cohesive failure due to insufficient elongation, it is also a candidate for crimping above the Tg of the polymer.

In some embodiments, after crimping, the polymer is then heated to set, anneal or otherwise remove internal stresses caused by mechanically stressing the polymer during assembly of the medical device. In some embodiments, the polymer is heated to an annealing temperature.

Figure 5:
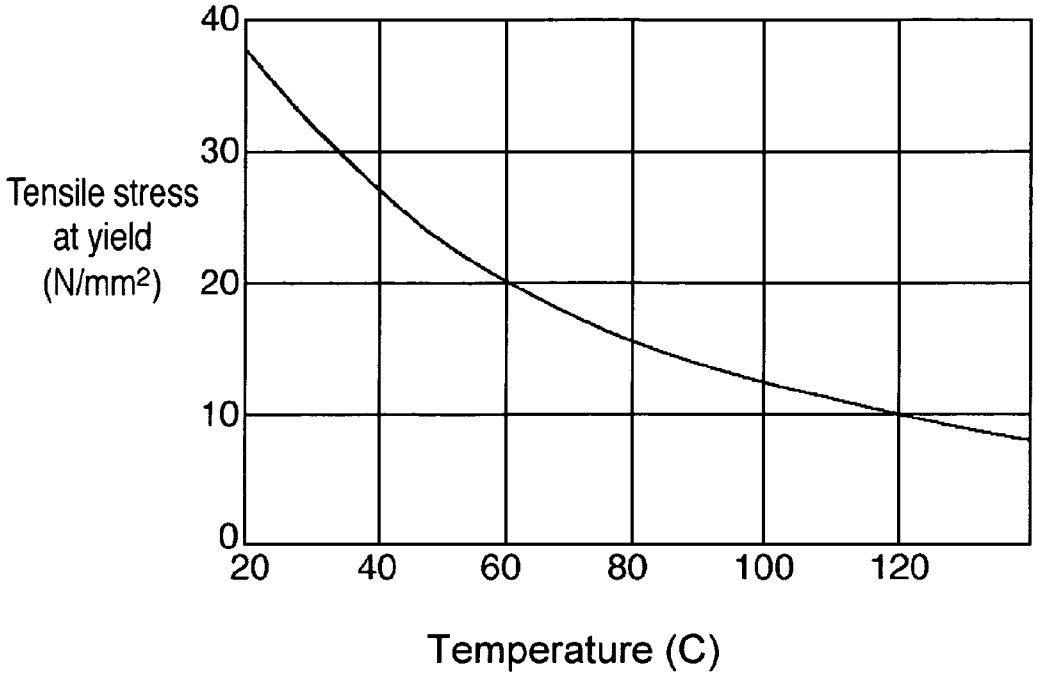
FIG. 5 shows the tensile stress at yield of polypropylene as a function of temperature.
Figure 6:
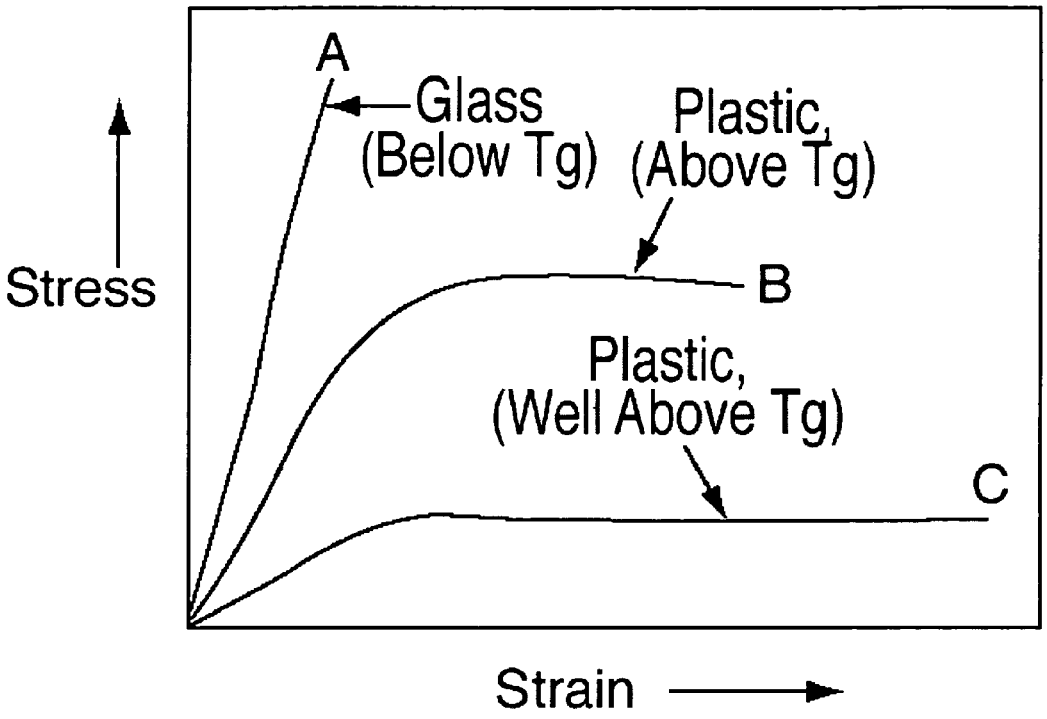
FIG. 6 shows how the stress-strain curve of a thermoplastic polymer changes with temperature.

FIG. 5 shows tensile stress at yield of polypropylene as a function of temperature. This property is not the same as hardness, but correlates with it. Both involve the stress needed to permanently deform the polymer. For thermoplastics in general, a lower temperature leads to greater hardness. FIG. 6 shows how a thermoplastic's stress-strain curve changes with temperature.

Figure 7:
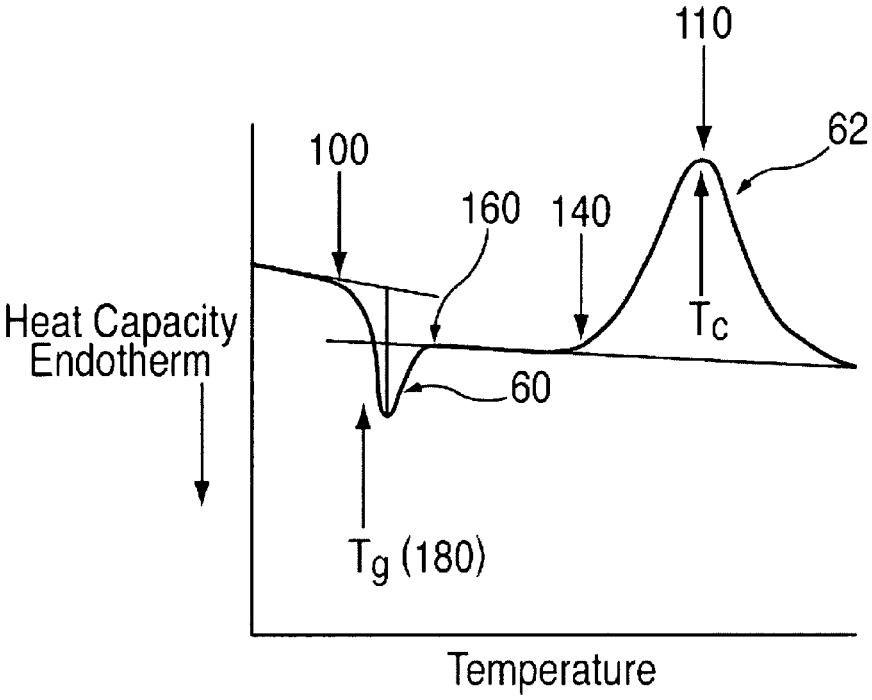
FIG. 7 plots heat capacity versus temperature for a typical thermoplastic polymer.
Figure 8:
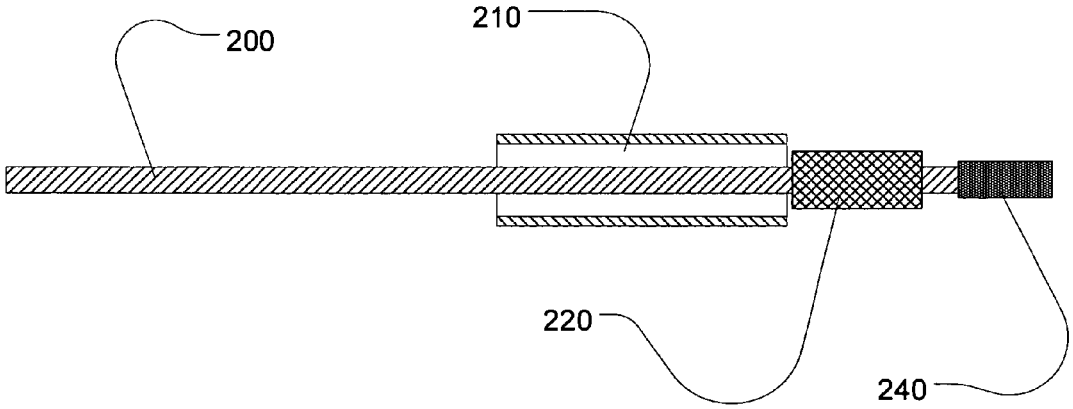
FIG. 8 shows a stent-delivery device combination, in cross-section.
Figure 9:
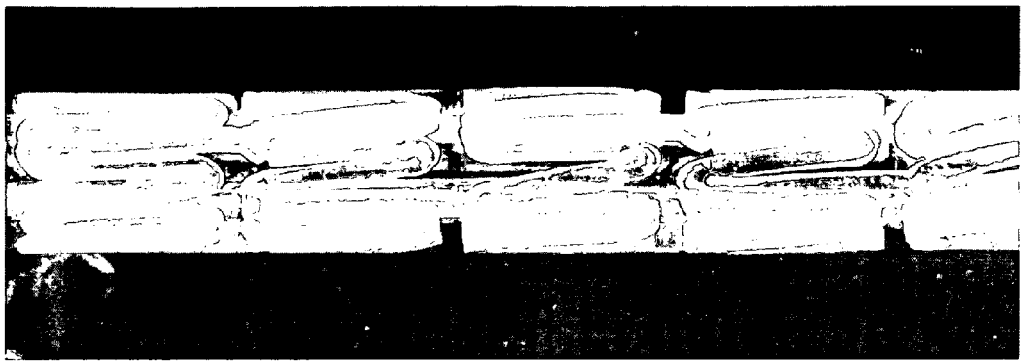
FIG. 9 shows a polymeric stent after heat crimping.

For some embodiments of this invention, the target temperature is selected in relation to Tg of the polymer. Tg is the temperature at which the amorphous domains of a polymer change from a brittle vitreous state to a plastic state at atmospheric pressure. In other words, Tg corresponds to the temperature where the onset of segmental motion in the chains of the polymer occurs, and it is discernible in a heat-capacity-versus-temperature graph for a polymer, as is depicted in FIG. 7. When an amorphous or semicrystalline polymer is heated, its coefficient of expansion and heat capacity both increase as the temperature rises, indicating increased molecular motion. As the temperature rises, the sample's actual molecular volume remains constant. Therefore, a higher coefficient of expansion points to a free volume increase of the system and increased freedom of movement for the molecules. The increasing heat capacity corresponds to increasing heat dissipation through movement.

Tg of a given polymer can be dependent on the heating rate and can be influenced by the thermal history of the polymer. Furthermore, polymer chemical structure heavily influences Tg by affecting polymer mobility. Generally, flexible main-chain components lower Tg and bulky side groups raise Tg. Similarly, increasing flexible-side-group length lowers Tg and increasing main-chain polarity increases Tg. Additionally, the presence of crosslinks can increase the observed Tg for a given polymer, and the presence of a drug or therapeutic agent can alter the Tg of a polymer due to plasticization effects. The magnitude of these plasticization effects depends on the miscibility and compatibility of the drug and polymer and the loading of drug in the polymer.

By way of illustration, when a semicrystalline polymer is heated, the polymer crystallinity begins to increase as temperature reaches Tg. At or above Tg, the increased molecular motion allows the polymer chains to adopt a more thermodynamically stable relationship, and thereby increases polymer crystallinity. In FIG. 7, Tg is shown on the first curve, 60, which is the temperature at which half of the increase in heat capacity has occurred. The crystallinity then increases rapidly after Tg and reaches a maximum at Tc (the apex of second curve, 62).

As can be seen in FIG. 7, Tg is somewhat arbitrarily placed on the temperature versus heat capacity curve. For purposes of this disclosure, the Tg range is defined in several different ways for a polymer or polymer combination. Some invention embodiments can be predicated on any one of these Tg range definitions.

Tg Range Definition 1

For this definition, Tg range is greater than or equal to the initial point on the polymer's (or polymer combination's) temperature-versus-heat-capacity curve showing a drop in heat capacity, indicated as Tg1 (100) on FIG. 7 (this point is defined as lower Tg for definition 1). Tg range is less than or equal to Tc (110) on the curve in FIG. 7 (this point is defined as upper Tg for definition 1). This Tg range is referred to in this disclosure as Tg range definition 1. Those of ordinary skill in the art recognize that the specific curvature and temperature points in FIG. 7 depend upon the nature of the polymer or polymer combination. Therefore, the indication of a point on FIG. 7 is meant to communicate a point corresponding to the FIG. 7 point on a similar graph for the particular polymer or polymer combination being used.

A target temperature is within Tg range definition 1 if it is above or equal to Tg1 and below or equal to Tg2. A target temperature is below Tg range definition 1 if it is below or equal to Tg2. A target temperature is above Tg range definition 1 if it is above or equal to Tg1. A target temperature is between a higher temperature and a lower temperature if it is above or equal to the lower temperature and below or equal to the higher temperature. These concepts hold for all temperatures and ranges throughout this disclosure.

Tg Range Definition 2

For this definition, the Tg range is greater than or equal to the point Tg1 (100) on FIG. 7 (lower Tg for definition 2) and less than or equal to point 140 on FIG. 7 (upper Tg for definition 2). This range is referred to in this disclosure as Tg range definition 2. Point 140 corresponds to the onset of the crystallization phase transition for the material.

Tg Range Definitions 3, 4, 5, and 6

For definition 3, the Tg range is the conventionally measured Tg (180) for the polymer (or combination) plus 40° C. (upper Tg for definition 3) and minus 40° C. (lower Tg for definition 3).

For definition 4, the Tg range is the conventionally measured Tg for the polymer (or combination) plus 20° C. (upper Tg for definition 4) and −20° C. (lower Tg for definition 4).

For definition 5, the Tg range is the conventionally measured Tg for the polymer (or combination) plus 10° C. (upper Tg for definition 5) and minus 10° C. (lower Tg for definition 5).

For definition 6, the Tg range is the conventionally measured Tg for the polymer (or combination) plus 5° C. (upper Tg for definition 6) and minus 5° C. (lower Tg for definition 6).

Tg Range Definition 7

For this definition, the Tg range is greater than or equal to the point Tg1 (100) on FIG. 7 (lower Tg for definition 7) and less than or equal to point 160 on FIG. 7 (upper Tg for definition 7). This range is referred to in this disclosure as Tg range definition 7. Point 160 corresponds to the tail off or end of the glass phase transition for the material.

These embodiments also include embodiments in which the Tg range specifically excludes ambient temperature, ambient temperature + or −1° C. or ambient temperature + or −5° C. Also, in some embodiments the target temperature has a maximum at or below the temperature at which any included therapeutic agents substantially decompose. For purposes of this disclosure, "substantially decompose" means decomposition to the extent that one of ordinary skill in the art would conclude that the decomposition would reduce the efficacy of the therapeutic substance too much. In other words, decomposition would reduce the efficacy enough that one of ordinary skill in the art would reject the heated or cooled, crimped composition for use in vivo.

Based on the shore hardness of the polymer or the failure mode of the coating or polymer, several embodiments can be described. For polymers that are too soft, that exhibit cohesive or deformation failures, that have Tg below ambient or room temperature, or that have a shore hardness of shore 60A to 80D (alternatively, shore 80A to 60D), the polymer can be improved by causing the polymer to be harder during crimping. This can be accomplished by choosing a target temperature less than upper Tg. (When this disclosure speaks of upper Tg or lower Tg, but does not specify which definition of Tg range is being used, this disclosure is intended to cover upper and lower Tg for each range definition). Alternatively, the polymer can be hardened during crimping by choosing a target temperature below lower Tg. Alternatively, choosing a target temperature below ambient temperature can harden the polymer. Alternatively, choosing a target temperature below −30° C., −40° C., −50° C., or −60° C. can harden the polymer. In some embodiments, the target temperature is between ambient temperature and upper Tg; ambient temperature and lower Tg; or −30° C., −40° C., −50° C., or −60° C. and upper Tg; −30° C., −40° C., 50° C., or −60° C. and lower Tg; or −30° C., −40° C., −50° C., or −60° C. and ambient temperature.

In addition to choosing the target temperature based on the Tg range definitions discussed above, various embodiments can be described otherwise. For polymers that are too soft, that exhibit cohesive or deformation failures, that have Tg below ambient or room temperature, or that have a shore hardness of shore 60A to 80D (alternatively, shore 80A to 60D), the polymer can be improved by causing the polymer to be harder during crimping. Therefore, an improvement in cohesive or deformation failures can be achieved by choosing a target temperature that yields a 50% increase in shore hardness, alternatively, a 40%, 30%, 20%, or 10% increase in shore hardness.

Medical devices that use polymers with shore hardness of shore 60A to 60D frequently experience cohesive failure during crimping. Invention medical devices prepared with invention crimping methods allow the use of polymers with shore D hardness as low as 30 to 80, or 35 to 60. Alternatively, invention medical devices prepared with invention crimping methods allow the use of polymers with shore D hardness less than or equal to 45, 40, 35, or 30.

For polymers that are too hard, that exhibit adhesive failures, have insufficient elongation, or that have Tg above ambient or room temperature, or that have a shore hardness of 60D to 95D (alternatively, 65D to 90D), the polymer can be improved by causing the polymer to be softer during crimping or by maintaining an increased temperature in the polymer after crimping to relieve any stress. This can be accomplished by choosing a target temperature greater than upper Tg. Alternatively, the target temperature is above lower Tg. Alternatively, the target temperature is above ambient temperature. Alternatively, the target temperature is above 70° C., 80° C., 90° C., or 100° C. In some embodiments, the target temperature is between ambient temperature and upper Tg; ambient temperature and lower Tg; between 70° C., 80° C., 90° C., or 100° C. and upper Tg; between 70° C., 80° C., 90° C., or 100° C. and lower Tg; or between 70° C., 80° C., 90° C., or 100° C. and ambient temperature.

In addition to choosing the target temperature based on the Tg range definitions discussed above, various embodiments can be described otherwise. For polymers that are too hard, that exhibit adhesive failures, that have Tg above ambient or room temperature, or that have a shore hardness of 60D to 95D (alternatively, 65D to 90D), the polymer can be improved by causing the polymer to be softer during crimping. Therefore, an improvement in adhesive failure can be achieved by choosing a target temperature that yields a 50% decrease in shore hardness, alternatively, a 40%, 30%, 20%, or 10% decrease in shore hardness.

Medical devices that use polymers with shore hardness of shore 60D to shore 90D frequently experience adhesive, or elongational failure during crimping. Invention medical devices prepared with invention crimping methods allow the use of polymers with shore hardness as high as 60D to 90D, or 65D to 85D. Alternatively, invention medical devices prepared with invention crimping methods allow the use of polymers with shore hardness greater than or equal to 60D, 70D, 80D, or 90D.

When EVAL is crimped at ambient temperature, it is in a glassy state (FIG. 6, curve A). By crimping at a temperature above its glass transition temperature (Tg) (55° C.), the ultimate elongation becomes higher (FIG. 6, curve B). This should reduce cracking in the tensile regions on the outside of stent junctions. For PBMA, Tg of 20° C., crimping at a low temperature of 0° or less should reduce crimping damage from shear and compression. Similarly, for KYNAR (a polymer consisting of poly(vinylidene fluoride) and available from Atofina of Philadelphia, Pa.), Tg of −30° C., crimping at a temperature of −40° C. should also reduce denting and shearing damage.

In some embodiments, a polymeric stent is crimped onto a delivery device, such as a catheter, after being heated to a target temperature. The target temperature is greater than Tg range for definitions 1-7, any of definitions 1-7, any combination of definitions 1-7, or any combination of definitions 1-7 that also excludes any one or any combination of definitions 1-7.

In some embodiments, a polymeric stent is crimped onto a delivery device, such as a catheter, while being heated to a target temperature. The target temperature is greater than Tg range for definitions 1-7, any of definitions 1-7, any combination of definitions 1-7, or any combination of definitions 1-7 that also excludes any one or any combination of definitions 1-7.

Devices for crimping medical devices are well known in the art. In some embodiments, the device is designed to crimp the polymer-coated stent onto the balloon portion of a catheter for PTCA. For crimpers such as the sliding wedge design, the temperature may be controlled by passage of a stream of dry air, or inert gas through the bore. This air can be heated or cooled by first passing it through a tube heater or chilled heat exchanger. The stent is loosely placed onto the catheter, and then the assembly is inserted into the bore of the crimper. The passage of air would rapidly equilibrate the stent delivery system (SDS) to the crimp temperature. Continuously heated or cooled airflow would bring the crimping jaws to the desired temperature.

Alternative ways include heating or cooling the jaws of the crimper itself. Electrical heating elements can be installed into the crimper jaws. By appropriate placement of thermocouples and feedback controls, an elevated temperature can be maintained. Cooling of the crimper jaws can be accomplished by rendering them with passageways through which a cooling medium is pumped. This may also be used to heat the crimping jaws. If the jaws were composed of an electrically conductive material, application of an oscillating electric field can heat them via eddy currents. If the jaws were made of an IR transparent material, the stent on catheter can be thermostated by infrared radiation.

If the crimper is at ambient temperature, but the jaws themselves are of a material with low thermal conductivity, then processes can be considered where the stent loosely applied to the catheter is pre-equilibrated to a non-ambient temperature before crimping. As the stent is small, with a high surface area to volume ratio, it would have to be rapidly moved from the controlled temperature environment to the crimper to maintain the desired temperature. Heating in an incubator or oven, or cooling in a refrigerator can pre-equilibrate the stent to the desired temperature before crimping.

Processes of the current invention provide medical devices. These medical devices contain a piece or portion that is coated with or constructed of, in some embodiments, polymer(s). In some embodiments, the crimping device used in invention crimping steps can be heated or cooled before it is used to crimp the piece or portion onto the remainder of the medical device or onto another medical device. This heating or cooling causes the temperature of the material to change so that the crimping effectively occurs at a target temperature other than ambient temperature. Other ways of modifying the temperature of the polymer include heating or cooling the substrate of the medical device or heating or cooling the material directly with forced air, among other methods.

Some invention embodiments select medical devices to be those adapted for placement in arterial, venous, neurovascular, urethral, biliary, prostate, intravascular, ureteral, bronchial, esophageal, fallopial, tracheal, laryngeal, gastrointestinal, lymphatic, eustachiaic, pancreatic, cerebral, other genitourinary, other gastrointestinal, or other respiratory lumens or passages.

Invention methods can be used on a variety of polymeric materials including those characterized as having Tg above ambient temperature. In some embodiments the methods act on polymeric materials comprising ABS resins; acrylic polymers and acrylic copolymers; acrylonitrile-styrene copolymers; alkyd resins; biomolecules; cellulose ethers; celluloses; copoly(ether-esters); copolymers of polycarboxylic acids and poly-hydroxycarboxylic acids; copolymers of vinyl monomers with each other and olefins; cyanoacrylates; epoxy resins; ethylene vinyl alcohol copolymers; ethylene-methyl methacrylate copolymers; ethylene-vinyl acetate copolymers; ethylene-α-olefin copolymers; poly(amino acids); poly (anhydrides); poly(butyl methacrylates); poly(ester amides); poly(ester-urethanes); poly(ether-urethanes); poly(imino carbonates); poly(orthoesters); poly(silicone-urethanes); poly(tyrosine arylates); poly(tyrosine-derived carbonates); polyacrylates; polyacrylic acid; polyacrylic acids; polyacrylonitrile; polyacrylonitrile; polyalkylene oxalates; polyamides; polyamino acids; polyanhydrides; polycarbonates; polycarboxylic acids; polycyanoacrylates; polyesters; polyethers; poly-hydroxycarboxylic acids; polyimides; polyisobutylene and ethylene-α-olefin copolymers; polyketones; polymethacrylates; polyolefins; polyorthoesters; polyoxymethylenes; polyphosphazenes; polyphosphoesters; polyphosphoester urethanes; polyphosphoesters; polyphosphoesters-urethane; polyurethanes; polyvinyl aromatics; polyvinyl esters; polyvinyl ethers; polyvinyl ketones; polyvinylidene halides; silicones; starches; vinyl copolymers vinyl-olefin copolymers; and vinyl halide polymers and copolymers.

Some embodiments select the group of polymers to specifically exclude any one of or any combination of the polymers listed above.

Specific examples of useful polymers for some embodiments include the following polymers: starch, sodium alginate, rayon-triacetate, rayon, polyvinylidene fluoride, polyvinylidene chloride, polyvinyl pyrrolidone, polyvinyl methyl ether, polyvinyl chloride, polyvinyl acetate, polystyrene, polyisocyanate, polyisobutylene, polyethylene glycol, polydioxanone, polycaprolactone, polycaprolactam, KYNAR (brand poly(vinylidene fluoride) available from Atofina), polyacrylonitrile, poly(trimethylene carbonate), poly(L-lactic acid), poly(lactide-co-glycolide), poly(hydroxyvalerate), poly(hydroxybutyrate-co-valerate), poly(hydroxybutyrate-co-hydroxyvalerate), poly(hydroxybutyrate), poly(glycolide), poly(glycolic acid), poly(D,L-lactide-co-L-lactide), poly(D,L-lactide-co-glycolide), poly(D,L-lactide), poly(4-hydroxybutyrate), poly(3-hydroxybutyrate), poly(3-hydroxy valerate), Nylon 66, hyaluronic acid, fibrinogen, fibrin, elastin-collagen, collagen, cellulose propionate, cellulose nitrate, cellulose butyrate, cellulose acetate butyrate, cellulose acetate, cellulose, cellophane, carboxymethyl cellulose, or poly(2-hydroxyethyl methacrylate), Chitin, Chitosan, EVAL, poly(butyl methacrylate), poly(D,L-lactic acid), poly(D,L-lactide), poly(glycolic acid-co-trimethylene carbonate), poly (hydroxybutyrate-co-valerate), poly(hydroxyvalerate), poly (iminocarbonate), poly(lactide-co-glycolide), poly(L-lactic acid), poly(N-acetylglucosamine), poly(trimethylene carbonate), poly(vinyl chloride), poly(vinyl fluoride), poly(vinylidene chloride), poly(vinylidene fluoride), poly(yinylidene fluoride-co-chlorotrifluoroethylene), poly (vinylidene fluoride-co-hexafluoropropene), polyanhydride, polyorthoester, polyurethane, polyvinyl alcohol, polyvinyl chloride, rayon, SOLEF 21508 (formulation available from Solvay Solexis), and PEO/PLA. Some embodiments select the group of polymers to specifically exclude any one of or any combination of the polymers listed above.

The polymer for use with this invention can comprise a mixture of polymers, such as an intimate mixture of polymer molecules, or can use a combination of polymers arranged in a layered structure. One of ordinary skill in the art will recognize that the optimal target temperature can be chosen based on the overall thermal behavior of the polymers or combination of polymers.

Some embodiments add conventional drugs, such as small, hydrophobic drugs, to invention polymers (as discussed in any of the embodiments, above), making them biostable, drug systems. Some embodiments graft-on conventional drugs or mix conventional drugs with invention polymers. Invention polymers can serve as base or topcoat layers for biobeneficial polymer layers.

The selected drugs can inhibit vascular, smooth muscle cell activity. More specifically, the drug activity can aim at inhibiting abnormal or inappropriate migration or proliferation of smooth muscle cells to prevent, inhibit, reduce, or treat restenosis. The drug can also include any substance capable of exerting a therapeutic or prophylactic effect in the practice of the present invention. Examples of such active agents include antiproliferative, antineoplastic, antiinflammatory, antiplatelet, anticoagulant, antifibrin, antithrombin, antimitotic, antibiotic, and antioxidant substances, as well as their combinations, and any prodrugs, metabolites, analogs, congeners, derivatives, salts and their combinations.

An example of an antiproliferative substance is actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin II, actinomycin X1, and actinomycin C1. Examples of antineoplastics include paclitaxel and docetaxel. Examples of antiplatelets, anticoagulants, antifibrins, and antithrombins include aspirin, sodium heparin, low molecular weight heparin, hirudin, argatroban, forskolin, vapiprost, prostacyclin and prostacyclin analogs, dextran, D-pheproarg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocor). Examples of antimitotic agents include methotrexate, azathioprine, vincristine, vinblastine, fluorouracil, adriamycin, and mutamycin. Examples of cytostatic or anti-proliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck & Co., Whitehouse Station, N.J.), calcium channel blockers (such as Nifedipine), colchicine, fibroblast growth factor (FGF) antagonists, histamine antagonist, LOVASTATIN (an inhibitor of HMG-CoA reductase, a cholesterol lowering drug from Merck &Co.), monoclonal antibodies (such as PDGF receptors), nitroprusside, phosphodiesterase inhibitors, prostaglandin inhibitor (available from Glazo), Seramin (a PDGF antagonist), serotonin blockers, thioprotease inhibitors, triazolopyrimidine (a PDGF antagonist), and nitric oxide. Other useful drugs may include alpha-interferon, genetically engineered epithelial cells, dexamethasone, estradiol, clobetasol propionate, cisplatin, insulin sensitizers, receptor tyrosine kinase inhibitors, and carboplatin. Exposure of the composition to the drug should not adversely alter the drug's composition or characteristic. Accordingly, drug containing embodiments choose drugs that are compatible with the composition. Rapamycin is a suitable drug. Additionally, methyl rapamycin (ABT-578), everolimus, 40-O-(2-hydroxy)ethyl-rapamycin, or functional analogs or structural derivatives thereof, is suitable, as well. Examples of analogs or derivatives of 40-O-(2-hydroxy) ethyl-rapamycin include, among others, 40-O-(3-hydroxy) propyl-rapamycin and 40-O-2-(2-hydroxy)ethoxyethylrapamycin. Those of ordinary skill in the art know of various methods and coatings for advantageously controlling the release rate of drugs, such as 40-O-(2-hydroxy)ethyl-rapamycin.

Some embodiments choose the drug such that it does not contain at least one of or any combination of antiproliferative, antineoplastic, antiinflammatory, antiplatelet, anticoagulant, antifibrin, antithrombin, antimitotic, antibiotic, or antioxidant substances, or any prodrugs, metabolites, analogs, congeners, derivatives, salts or their combinations.

Some invention embodiments choose the drug such that it does not contain at least one of or any combination of actinomycin D, derivatives and analogs of Actinomycin D, dactinomycin, actinomycin IV, actinomycin II, actinomycin X1, actinomycin C1, paclitaxel, docetaxel, aspirin, sodium heparin, low molecular weight heparin, hirudin, argatroban, forskolin, vapiprost, prostacyclin, prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor and 7E-3B, methotrexate, azathioprine, vincristine, vinblastine, fluorouracil, adriamycin, mutamycin, angiopeptin, angiotensin converting enzyme inhibitors, CAPTOPRIL, CILAZAPRIL, or LISINOPRIL, calcium channel blockers, Nifedipine, colchicine, fibroblast growth factor (FGF) antagonists, histamine antagonist, LOVASTATIN, monoclonal antibodies, PDGF receptors, nitroprusside, phosphodiesterase inhibitors, prostaglandin inhibitor, Seramin, PDGF antagonists, serotonin blockers, thioprotease inhibitors, triazolopyrimidine, nitric oxide, alpha-interferon, genetically engineered epithelial cells, dexamethasone, estradiol, clobetasol propionate, cisplatin, insulin sensitizers, receptor tyrosine kinase inhibitors, carboplatin, Rapamycin, 40-O-(2-hydroxy)ethyl-rapamycin, or a functional analogs of 40-O-(2-hydroxy)ethyl-rapamycin, structural derivative of 40-O-(2-hydroxy)ethyl-rapamycin, 40-O-(3-hydroxy)propyl-rapamycin, and 40-O-2-(2-hydroxy)ethoxyethyl-rapamycin, or any prodrugs, metabolites, analogs, congeners, derivatives, salts or their combinations.

Some invention embodiments comprise a drug or drug combination, and some require a drug or combination of drugs. Of the drugs specifically listed above, some invention embodiments exclude a single or any combination of these drugs.

Some embodiments comprise polymers combined with other polymers in multilayer arrangements. For example, one polymer can under- or over-lay another polymer such as a polymer coated on a device, a medical device, an implantable medical device, or a stent. The polymer can be used neat in this regard, or it can first be mixed with another polymer.

Examples of implantable devices useful in the present invention include self-expandable stents, balloon-expandable stents, and stent-grafts. The underlying structure of the device can be of virtually any design. The device can comprise a metallic material or an alloy such as, but not limited to, cobalt chromium alloy (ELGILOY), stainless steel (316 L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium, and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Of course, one of ordinary skill in the art recognizes that the invention method is only useful for medical devices that use a crimping step in their production.

Various, specialized tests are used to assay the integrity of a drug eluting stent coating. In all of them, completed units are tested which have been though all stent-catheter assembly processes, including crimping and any heat-pressure processes. One test is inspection of the coated stents by scanning electron microscopy. This can be done on the completed units by cutting the stent-balloon section from the catheter, or the stent can be removed from the catheter by dry expansion in air or wet expansion in aqueous solution. Under SEM, the fraction of compromised coating surface area can be estimated. Compromised coating is coating that has been deformed, torn, or removed. When this fraction of surface area exceeds 5-10%, the drug-release rate properties, and total drug content can be affected. Another measure of coating integrity, which is tied to crimping damage, is the number and size of particles shed when the stent is expanded in aqueous solution. The stent is deployed in a solution of previously filtered water and the particles shed are counted by one of several available particle-counting instruments. Example instruments would be those produced by Malvern that work by light scattering, instruments that work by light obscuration, such as the Hiac-Royco, or the Coulter counter which works by electrical conductivity. Elevated numbers, and sizes, of particles shed are indicative of coating failure, which is affected by crimping damage either in the form of coating pieces that are completely shorn off, or cracks in the coating which propagated during stent expansion to liberate particles. Yet another approach to measuring the effects of coating crimping damage is by acute thrombogenicity testing, one example of which is that detailed by Sukavaneshvar et al. ASIAO Journal, Aug. 11, 2000, p 301 and ASIAO Journal, Jul. 5, 2000, p M393, which approach subjected stents deployed in tubing to a flow of bovine blood in which the platelets have been radiolabeled. Accumulation of platelets and thrombus is a measure of the acute thrombogenicity. The effect of coating cracks and defect can be compared to uncoated stents, or to stents where the coatings have fewer, or no cracks and coating defects.

EXAMPLES

Example 1

Used to Make Stents for FIGS. 1&2

A first composition was prepared by mixing the following components:

(a) 2.0 mass % of poly(ethylene-co-vinyl alcohol) (EVAL) EC-151A and (b) the balance, dimethylacetamide The first composition was applied onto the surface of bare 13 mm TETRA stents (available from Guidant Corporation), which were first pre-expanded by passing them over a 0.071 inch, tapered mandrel. Coating was sprayed and dried to form a primer layer. A spray coater was used having a 0.046 fan nozzle maintained at about 60 C with a feed pressure 2.5 psi (0.17 atm) and an atomization pressure of about 15 psi (1.02 atm). Coating was applied at 10 μg per pass, in between which the stent was dried for 10 seconds in a flowing air stream at 60 C. Approximately 70 μg of wet coating was applied. The stents were baked at 140 C for one hour, yielding a primer layer composed of approximately 50 μg of EVAL.

A simulated reservoir layer was applied onto the primer layer, using the same spraying technique, equipment, and formulation used for the applying the primer. In this case, approximately 340 μg of wet coating is applied, followed by drying, e.g., baking at 50 C for about two hours, yielding about 300 μg of simulated drug-polymer reservoir layer.

A second composition can be prepared by mixing the following components:

(a) 2.0 mass % of Elast-Eon 80A and (b) the balance dimethylacetamide.

The second composition can be applied onto the dried simulated drug reservoir layer to form a topcoat layer. Using the same spraying technique and equipment used for applying the simulated drug reservoir layer. Approximately 340 μg of wet topcoat is applied followed by baking at 80 C for two hours, yielding a 300 μg Elast-Eon 80A topcoat layer.

Using a sliding wedge crimper, the stents were crimped onto 13 mm Tetra catheters (available from Guidant Corporation). The stents were expanded in deionized water at 37 C with a balloon deployment pressure of 12 atm. Examination by SEM yielded FIGS. 1 &2.

Example 2

Used to Make Stents for FIG. 3

A first composition was prepared by mixing the following component (a) 4.0 mass % of poly(ethylene-co-vinyl alcohol) (EVAL) EC-151A and (b) the balance, an 80/20 weight blend of dimethylacetamide and pentane.

The first composition was applied onto the surface of bare 13 mm TETRA stents (available from Guidant Corporation), which were first pre-expanded by passing them over a 0.071 inch, tapered mandrel. Coating was sprayed and dried to form a primer layer. A spray coater was having a 0.046 fan nozzle maintained at about 60 C with a feed pressure 2.5 psi (0.17 atm) and an atomization pressure of about 15 psi (1.02 atm). Coating was applied at 10 μg per pass, in between which the stent was dried for 10 seconds in a flowing air stream at 60 C. Approximately 65 μg of wet coating was applied. The stents were baked at 140 C for one hour, yielding a primer layer composed of approximately 60 μg of EVAL.

A simulated reservoir layer was applied onto the primer layer, using the same spraying technique, equipment, and formulation used for the applying the primer. In this case approximately 340 μg of wet coating is applied, followed by drying, e.g., baking at 80 C for about two hours, yielding about 315 μg of a simulated drug-polymer reservoir layer.

A second composition can be prepared by mixing the following components:

(a) 2.0 mass % of Solef 21508 and (b) the balance a 50/25/25, by weight, blend of acetone, cyclohexanone, and AMS Defluxer.

AMS Defluxer is a blend of dichloropentafluoropropanes and methanol available from Tech Spray Inc. of Amarillo Tex.

The second composition can be applied onto the dried simulated drug reservoir layer to form a topcoat layer. Using the same spraying technique and equipment used for applying the simulated drug reservoir layer. Approximately 345 μg of wet topcoat is applied followed by baking at 50 C for two hours, yielding a 325 μg Solef 21508 topcoat layer.

Using a sliding wedge crimper, the stents were crimped onto 13 mm Tetra catheters (available from Guidant Corporation). After this, they were subjected to a heat and pressure process wherein the balloon was restrained by a sheath, air pressure was applied to the catheter, and heat was applied to the balloon. Units were packaged and sterilized by electron beam radiation at a dose of 35 KGy. The stent coating performance was evaluated in an apparatus where a guiding catheter was connected to flexible silicone tubing embedded in a block with three gradual 90-degree bends. Deionized water at 37 C was recirculated through the guiding catheter. The stents were passed through a rotating hemostatic valve attached to the guiding catheter, through the guiding catheter, through the tortuous silicone tubing, and deployed at a pressure of 12 atmospheres. After the stents were removed from the tubing, examination by SEM yielded FIGS. 3 & 4.

Example 3

Figure 10:
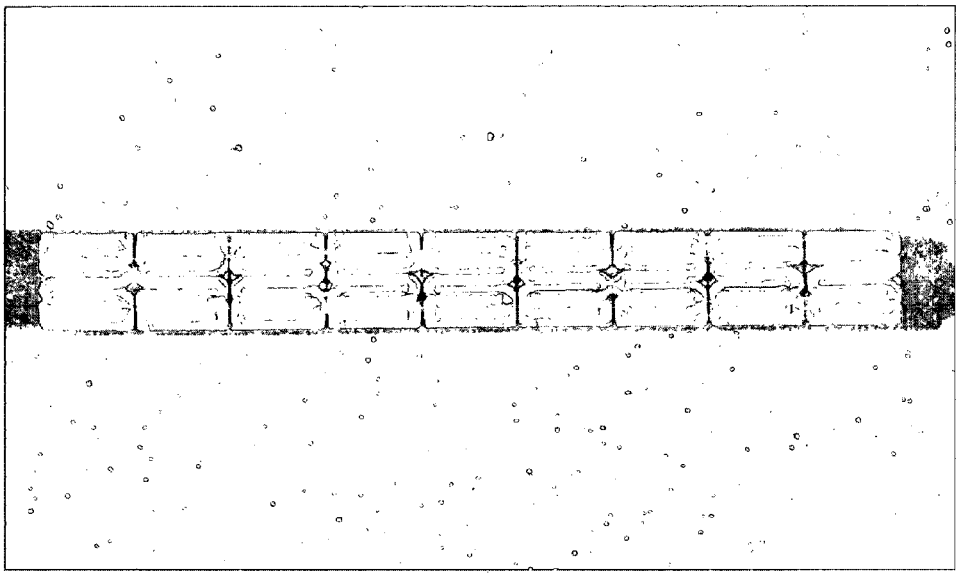
FIG. 10 shows the polymeric stent of Ex. 3 after heat crimping.

Used to make the Stent Shown in FIG. 10

Stents are laser cut from polymer tubing, then crimped to the desired diameter. A sliding wedge style heated crimper is used. The stents are supported on a wire mandrel during the crimping process.

| Parameters: | |
|---|---|
| Tubing material: | 100% poly(L-lactide) |
| Tubing OD: | 0.084" |
| Tubing ID: | 0.070" |
| Pre-heat temp: | 30 C. |
| Pre-heat time: | 30 seconds |
| Crimp temperature: | 30 C. |
| Descent time: | 3-5 seconds |
| Mandrel diameter: | 0.031" |
| Post crimp dwell time: | 99.9 seconds |
| Number of crimp cycles: | 1 |

Appropriate standards for the measurement of durometer hardness are ASTM D2240 or ISO868.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention. Additionally, various embodiments have been described above. For convenience's sake, combinations of aspects composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists that specifically excludes that aspect. All patents, test procedures, and other documents cited in this specification are fully incorporated by reference to the extent that this material is consistent with this specification and for all jurisdictions in which such incorporation is permitted.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically exclude the value or the conditions for the aspect.

What is claimed is:

1. A method of making a medical device comprising:

providing a stent cut from a tubing made of a polymer combination comprising poly(L-lactide);

positioning the stent loosely over a catheter; *and* crimping the positioned stent to secure the stent to [a] *the* catheter, wherein the crimping reduces the diameter of the stent[,]*;* wherein the temperature of the stent [substrate] during the crimping is [at a temperature between 10° C. below] *less than* the conventionally measured glass transition temperature for poly(L-lactide) (Tg) and [below] *greater than or equal to 10° C. less than* Tg.

2. The method of claim 1, wherein the method further comprises annealing the stent at a second temperature after securing the stent to the catheter.

3. The method of claim 1, wherein the temperature is [between 5° C. below Tg and below] *less than Tg and greater than or equal to 5° C. less than* Tg.

4. The method of claim 1, wherein the temperature of the stent during crimping is adjusted by thermal contact with a heat source.

5. The method of claim 1, wherein the crimping comprises applying radial compression pressure to the stent to reduce the diameter.

6. The method of claim 1, wherein the temperature is [between 2° C. below Tg and below] *less than Tg and greater than or equal to 2° C. less than* Tg.

*7. The method of claim 1, wherein the polymer combination is poly(L-lactide).*

*8. The method of claim 1, wherein the polymer combination is selected from a group consisting of: a mixture of more than one polymer, one polymer, and a copolymerization of more than one polymer.*

* * * * *